United States Patent
Korlach et al.

(10) Patent No.: US 9,347,900 B2
(45) Date of Patent: May 24, 2016

(54) REAL-TIME REDOX SEQUENCING

(71) Applicant: Pacific Biosciences of California, Inc., Menlo Park, CA (US)

(72) Inventors: Jonas Korlach, Newark, CA (US); Stephen Turner, Menlo Park, CA (US); Lei Sun, San Jose, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 110 days.

(21) Appl. No.: 13/652,172

(22) Filed: Oct. 15, 2012

(65) Prior Publication Data

US 2013/0109577 A1    May 2, 2013

Related U.S. Application Data

(60) Provisional application No. 61/547,557, filed on Oct. 14, 2011, provisional application No. 61/624,148, filed on Apr. 13, 2012.

(51) Int. Cl.
| | | |
|---|---|---|
| *C12Q 1/68* | (2006.01) | |
| *C40B 60/10* | (2006.01) | |
| *G01N 27/26* | (2006.01) | |
| *G01N 27/00* | (2006.01) | |
| *G01N 27/327* | (2006.01) | |

(52) U.S. Cl.
CPC ............ *G01N 27/00* (2013.01); *C12Q 1/6869* (2013.01); *G01N 27/3278* (2013.01); *C12Q 2521/543* (2013.01); *C12Q 2563/113* (2013.01); *C12Q 2565/607* (2013.01); *C40B 60/10* (2013.01)

(58) Field of Classification Search
None
See application file for complete search history.

(56) References Cited

U.S. PATENT DOCUMENTS

| | | | |
|---|---|---|---|
| 2009/0170716 A1* | 7/2009 | Su et al. ........................ 506/9 |
| 2012/0196279 A1 | 8/2012 | Underwood et al. | |
| 2012/0322666 A1 | 12/2012 | Pham et al. | |
| 2013/0138358 A1 | 5/2013 | Tang et al. | |
| 2013/0303385 A1 | 11/2013 | Korlach et al. | |
| 2013/0316912 A1 | 11/2013 | Bjornson et al. | |
| 2013/0322692 A1 | 12/2013 | Guan | |
| 2013/0327644 A1 | 12/2013 | Turner et al. | |

OTHER PUBLICATIONS

International Search Report and Written Opinion date Mar. 28, 2013 for related PCT/2012/060275.
International Preliminary Report on Patentability dated Apr. 24, 2014 for related PCT/2012/060275.

* cited by examiner

*Primary Examiner* — Samuel Woolwine
*Assistant Examiner* — Kaijiang Zhang
(74) *Attorney, Agent, or Firm* — Robert H. Reamey

(57) ABSTRACT

Real time redox sequencing methods, devices, and systems are described. Arrays of redox devices comprising one or two electrodes are used to provide sequence information about a template nucleic acid in a polymerase-template complex bound proximate to the electrode(s). A sequencing reaction mixture comprising nucleotide analogs comprising redox labels is introduced to the array of redox devices under conditions of polymerase mediated nucleic acid synthesis. The time sequence of incorporation of nucleotide analogs is determined by electrochemically identifying the redox labels of the nucleotide analogs that are incorporated into the growing strand.

10 Claims, 12 Drawing Sheets

REAL-TIME REDOX SEQUENCING

CROSS-REFERENCE TO RELATED APPLICATIONS

This application claims the benefit of priority to Provisional Application No. 61/547,557, filed Oct. 14, 2011, and Provisional Application No. 61/624,148, filed Apr. 13, 2012, the full disclosures of which are incorporated herein by reference in their entirety for all purposes.

STATEMENT REGARDING FEDERALLY SPONSORED RESEARCH

Not Applicable.

BACKGROUND OF THE INVENTION

Nucleic acid sequence data is valuable in myriad applications in biological research and molecular medicine, including determining the hereditary factors in disease, in developing new methods to detect disease and guide therapy (van de Vijver et al. (2002) "A gene-expression signature as a predictor of survival in breast cancer," New England Journal of Medicine 347: 1999-2009), and in providing a rational basis for personalized medicine. Obtaining and verifying sequence data for use in such analyses has made it necessary for sequencing technologies to undergo advancements to expand throughput, lower reagent and labor costs, and improve accuracy (See, e.g., Chan, et al. (2005) "Advances in Sequencing Technology" (Review) Mutation Research 573: 13-40 which is incorporated herein in its entireties for all purposes.

Various methods of sequencing are used and each has its strengths and weaknesses. Single molecule real time sequencing has advantages over other sequencing methodologies including the ability to provide longer read lengths. Many current methods of sequencing use optical labels. There is a need for improved sequencing instruments and methods that use non-optical readouts, and in particular real time single molecule sequencing methods with these characteristics.

Redox detection of single molecules, involving detecting the oxidation and reduction of molecules has been demonstrated. The current invention provides instruments, devices and methods for non-optical real time single molecule sequencing.

BRIEF SUMMARY OF THE INVENTION

In some aspects, the invention provides a method for nucleic acid sequencing comprising: providing a substrate comprising an oxidizing nanoscale electrode and a reducing nanoscale electrode, the substrate comprising a polymerase enzyme complex comprising a polymerase enzyme and a template nucleic acid, the complex attached to the substrate proximate to the electrodes; exposing the polymerase to a plurality of types of nucleotide analogs each comprising a different redox label attached to the phosphate portion of the nucleotide analog through a linker under conditions whereby polymerase mediated nucleic acid synthesis occurs, resulting in the growth of a nascent nucleic acid strand; applying voltages over time at the oxidizing nanoscale electrode and reducing nanoscale electrode, whereby when a nucleotide analog resides in the active site of the enzyme, a redox label is oxidized by the oxidizing nanoscale electrode, and reduced by the reducing nanoscale electrode; monitoring the current at the oxidizing nanoscale electrode and at the reducing nanoscale electrode over time, whereby the current from multiple oxidations and reductions of a redox label at the electrodes indicates an incorporation event for a nucleotide analog having a specific redox label; and using the monitored current at the electrodes over time to determine a sequence of the template nucleic acid.

In some embodiments the voltage of the oxidizing nanoscale electrode and the voltage of the reducing nanoscale electrode are each repeatedly brought to different voltage levels, whereby the current measured at each voltage level is used to identify a specific redox label. In some embodiments the voltages applied to the electrodes comprise sine waves, triangular waves or a saw tooth waves.

In some embodiments the polymerase is exposed to four types of nucleotide analogs, corresponding to A, G, C, T, or A, G, C, U, wherein the voltage of the oxidizing nanoscale electrode and the voltage of the reducing nanoscale electrode are each repeatedly brought to at least 4 different voltage levels. In some embodiments the amount of current over time is used to identify which type of nucleotide is incorporated. In some embodiments the characteristics of the current over time is used to identify which type of nucleotide is incorporated. In some embodiments the characteristic of the current over time includes the current oscillation color.

In some embodiments the enzyme is attached to the substrate between the electrodes.

In some embodiments the plurality of types of nucleotide analogs comprises four differently labeled nucleotide analogs 1, 2, 3, and 4, wherein nucleotide analogs 1 and 2 each comprise a redox label with a first type of redox moiety, and nucleotide analogs 3 and 4 each comprise redox label with a second type of redox moiety, wherein nucleotide 1 has a different number of redox moieties than nucleotide analog 2, and nucleotide 3 has a different number of redox moities than nucleotide analog 4.

In some aspects, the invention provides a method for nucleic acid sequencing comprising: providing a substrate comprising a nanoscale redox electrode, the substrate comprising a polymerase enzyme complex comprising a polymerase enzyme and a template nucleic acid, the complex attached to the nanoscale electrode or to the substrate proximate to the nanoscale electrode; exposing the polymerase to a plurality of types of nucleotide analogs each comprising a different redox label attached to the phosphate portion of the nucleotide analog through a linker under conditions whereby polymerase mediated nucleic acid synthesis occurs, resulting in the growth of a nascent nucleic acid strand; wherein the nanoscale electrode is repeatedly brought to a plurality of voltage levels comprising at least one oxidizing voltage and to at least one reducing voltage; applying voltages over time to the nanoscale redox electrode, whereby when a nucleotide analog resides in the active site of the enzyme, the redox label is oxidized and reduced by the nanoscale electrode; monitoring the current at nanoscale electrode at the plurality of voltages over time, whereby the current from multiple oxidations and reductions of a redox label at the electrode indicates an incorporation event for a nucleotide analog having a specific redox label; and using the monitored current at the electrode over time to determine a sequence of the template nucleic acid.

In some embodiments the voltage of the nanoscale electrode is repeatedly brought to different voltage levels, whereby the current measured at each voltage level is used to identify a specific redox label. In some embodiments the polymerase is exposed to four types of nucleotide analogs corresponding to A, G, C, T, or A, G, C, U, wherein the voltage of the nanoscale electrode is repeatedly brought to at least 8 different voltage levels. In some embodiments the voltages applied to the electrode comprise a sine wave, a triangular wave, or a saw tooth wave.

In some embodiments the amount of current over time is used to identify which type of nucleotide is incorporated. In some embodiments the characteristics of the current over time is used to identify which type of nucleotide is incorporated. In some embodiments characteristic of the current over time includes the current oscillation color. In some embodiments the enzyme is attached to the nanoscale redox electrode.

In some aspects, the invention provides a chip for sequencing a plurality of single nucleic acid template molecules comprising: a substrate comprising; a plurality of redox devices, each redox device comprising at least one nanoscale redox electrode and a single polymerase enzyme complex bound to the substrate proximate to the nanoscale redox electrode, wherein the polymerase enzyme complex comprises a polymerase enzyme and a template nucleic acid; wherein the substrate is configured such that the redox device comes into contact with a sequencing reaction mixture comprising a plurality of types of nucleic acid analogs each having a different redox labels; and a plurality of electrical connection sites for bringing current and voltage to the redox devices, and for receiving electrical signals from the devices.

In some embodiments the substrate comprises greater than 1,000 redox devices. In some embodiments the substrate comprises greater than 10,000 redox devices. In some embodiments the substrate comprises about 1,000 redox devices to about 10 million devices. In some embodiments the substrate comprises about 10,000 redox devices to about 1 million devices.

In some embodiments each nanoscale redox electrode is electrically connected to an electrical interconnection through which the electrode is brought to the appropriate voltage levels and through which the redox current is measured. In some embodiments the substrate comprises electronic elements for one or more of: providing current to bring the nanoscale electrodes to the desired voltages, measuring the redox current at the nanoscale electrodes, analog to digital conversion, signal processing, and data storage. In some embodiments the electrical elements are CMOS elements. In some embodiments the substrate comprises a plurality of counter electrodes. In some embodiments there is one counter electrode for each nanoscale redox device.

In some aspects, the invention provides a system for sequencing a template nucleic acid comprising: a housing having housing electrical connection sites; a chip that reversibly mates with the housing comprising a substrate comprising; chip electrical connection sites that reversibly connect to the housing electrical connection sites; a plurality of redox devices, each redox device comprising at least one nanoscale redox electrode and a single polymerase enzyme complex bound to the at least one nanoscale redox electrode or to the substrate proximate to the at least one nanoscale redox electrode, wherein the polymerase enzyme complex comprises a polymerase enzyme and a template nucleic acid; a fluid reservoir for contacting a sequencing reaction mixture with the redox devices, the sequencing reaction mixture comprising a plurality of types of nucleic acid analogs, each having a different redox label, wherein the redox labels are oxidized and reduced while an analog is associated with the polymerase enzyme complex; an electronic control system electrically connected to the nanoscale electrodes through the electrical connections to apply desired voltages to the nanoscale redox electrodes and for determining the current to and from the nanoscale redox electrodes; and a computer that receives information on the current to and from the nanoscale redox electrodes over time and uses such information to identify a sequence of the template nucleic acid.

In some embodiments the substrate comprises greater than 1,000 redox devices. In some embodiments the substrate comprises greater than 10,000 redox devices. In some embodiments the substrate comprises about 1,000 redox devices to about 10 million devices. In some embodiments the substrate comprises about 10,000 redox devices to about 1 million devices.

In some embodiments each nanoscale redox electrode is electrically connected to an electrical interconnection through which the electrode is brought to the appropriate voltage levels and through which the redox current is measured.

In some embodiments the substrate comprises electronic elements for one or more of: providing current to bring the nanoscale electrodes to the desired voltages, measuring the redox current at the nanoscale electrodes, analog to digital conversion, signal processing, and data storage. In some embodiments the electrical elements are CMOS elements. In some embodiments the substrate comprises a plurality of counter electrodes. In some embodiments there is one counter electrode for each nanoscale redox device.

BRIEF DESCRIPTION OF THE DRAWINGS

FIGS. 1(A), 1(B), 1(C), 1(D), 1(E), and 1(F) show redox sequencing steps.

FIGS. 2(A), 2(B), 2(C), 2(D), 2(E), and 2(F) show redox sequencing steps.

FIGS. 7(A), 7(B), 7(C), 7(D) and 7(E) show cross sections of structures formed at various stages of the process. 7(F) shows an alternate embodiment of the structure of the redox device at the end of the process.

DETAILED DESCRIPTION OF THE INVENTION

Figure 1:
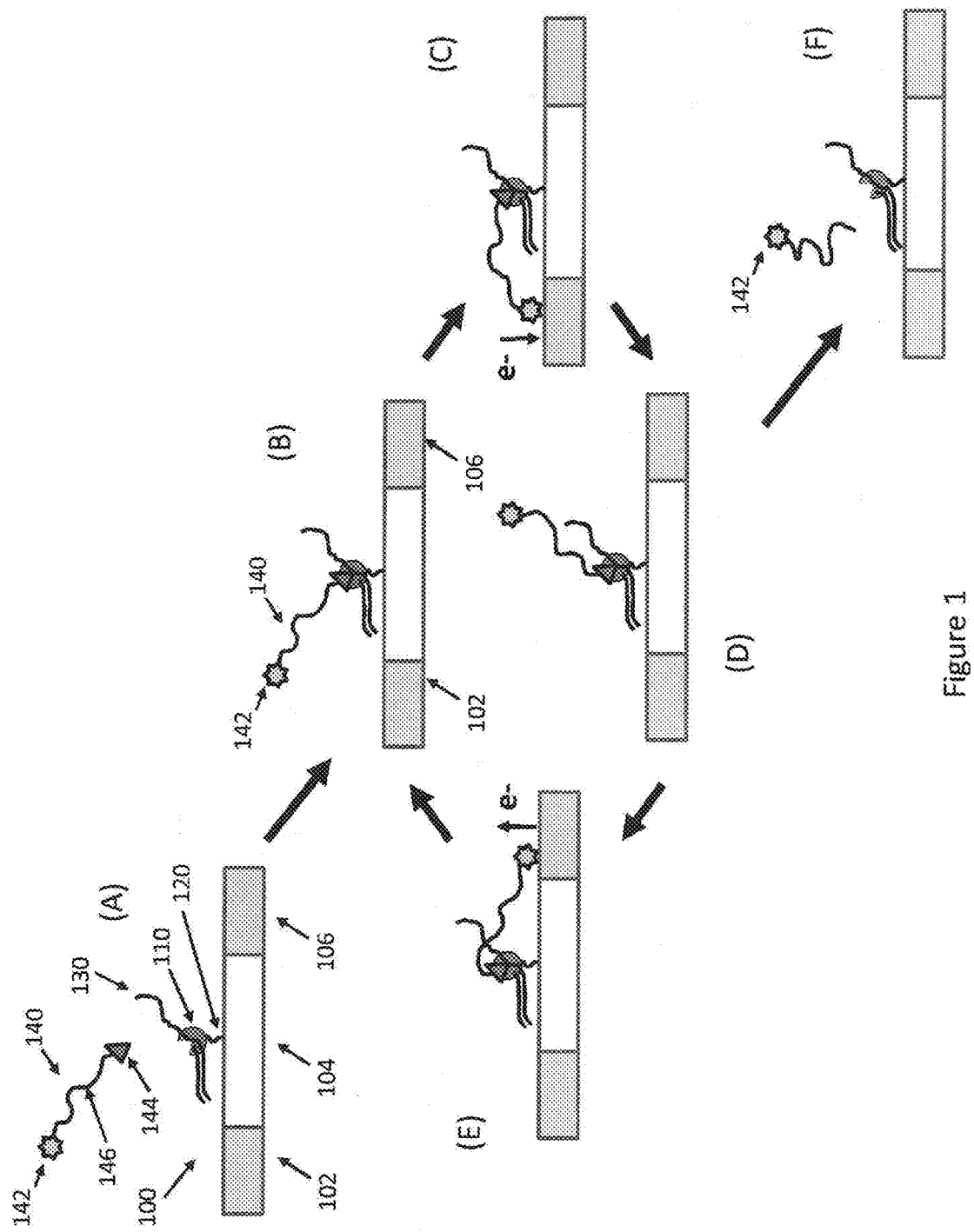
FIG. 1 shows an embodiment of the invention in which single molecule sequencing is carried out using a nanoscale redox device with two nanoscale working electrodes.

In some aspects, the invention provides methods, devices, systems, and compositions of matter directed to single molecule real time electrochemical sequencing. A single polymerase-template complex is immobilized proximate to one or two redox electrodes, and the incorporation of nucleotides by the polymerase enzyme is monitored by measuring the redox current from reducing and oxidizing a label on a nucleotide analog while it is held in the active site of the enzyme during incorporation. Typically, the redox electrodes are on the nanometer scale which allows for obtaining low capacitance, and to provide for adequate signal to noise.

Typically four nucleotide analogs, each having a different distinguishable redox label, are present. The redox label is connected to the analog through the phosphate portion of the nucleotide analog such that when the nucleotide analog is incorporated by the polymerase enzyme into the growing strand, the redox label is released. The redox label is connected to the nucleotide portion of the analog through a liker which has a length such that the redox label comes into contact with the one or two electrodes and become reduced and oxidized multiple times when the nucleotide analog is held in the polymerase enzyme active site. The current from repeated oxidation and reduction can be used to determine the presence and the identity of the nucleotide analog that is in the active site. The characteristics of the redox current while the nucleotide is in the active site will be different than the characteristics of a nucleotide that freely diffuses near the electrode. Because the nucleotide is held close to the electrodes during the incorporation process, it is subject to repeated excursions near enough to the electrode for electrochemical oxidation to occur over and over.

The voltage applied to the one or two nano-electrodes is typically varied over time in a manner that allows for the identification of the nucleotide analog in the active site using redox labels with different redox potentials. Base calling software can be used to call bases by correlating the redox current at the relevant voltage with the expected characteristics of the redox labels. The called bases can be used to identify the sequence of the template nucleic acid whose sequence is complementary to that of the added bases. The methods of the invention utilize the characteristic that a nucleotide analog which is incorporated spends more time in the active site of the enzyme and therefore spends more time proximate to the electrode than do non-cognate nucleotides that are not incorporated or freely diffusing nucleotides passing near the electrode.

Having a tethered redox label for detection provides for significant advantages over other redox detection methods. The tethered redox label is only able to sample a small region of space due to the fact that it is held by to the surface through the immobilized polymerase complex through the nucleotide analog that is in the active site of the polymerase enzyme during the incorporation process. Because the species to be detected samples such a small region, the size of the electrode required to detect the redox label is small, on the order of nanometers. Since the electrode is small, it therefore has a small area exposed to the solution. A small electrode area exposed to the solution means a limited area for reacting with solution components and resulting in noise. The tethered component can repeatedly come into contact with the nanoscale electrode, providing for higher signal to noise for these devices. For the two electrode configuration described herein, the repeated oxidations and reductions can occur at a fixed voltage by having the tethered redox label reach each electrode multiple times. For the one electrode configuration, multiple oxidations and reduction can occur for the tethered redox label by varying the voltage on the electrode from reducing to oxidizing on a time scale that is generally longer than the mean time for the redox label to diffuse into a region in which it will undergo a redox reaction.

Chips having arrays of nanoscale electrode redox devices are described. Each redox device performing a sequencing reaction in real time, allowing for hundreds, thousands, millions, or more sequencing reactions to be monitored simultaneously. The small size and the structure of the nanoscale electrodes are typically constructed to have low capacitance in order to allow for rapid transfer of current for electrochemical measurements on the microsecond to millisecond timescale. The chips can be prepared using known semiconductor processing techniques, for example on a silicon substrate. The nanoscale electrodes in the array have a polymerase enzyme-template complex attached proximate to them. The polymerase-template complex is close enough to the nanoscale electrode that a redox label on a nucleotide analog can be detected when the nucleotide analog is associated with the polymerase enzyme in the complex.

Systems for carrying out sequencing are described. The redox sequencing chips of the invention mate with a socket that holds the chip in place and provides electrical connections to interconnects on the chips for transferring electrical signals to and from the nanoscale electrodes. A current/voltage source provides the current and voltage to bring the nanoscale electrodes to the desired voltage as a function of time. A current meter measures the current to and from the nanoscale electrodes, allowing for the measurement of oxidation and reduction at the nanoscale electrodes.

The system includes a fluid reservoir for holding the sequencing reagents in contact with the nanoscale electrodes on the chip. The fluid reservoir can be, for example, a microfluidic chamber or a well. The system also has either a counter electrode, a reference electrode or both in contact with the fluid. The counter electrode and or the reference electrode can be incorporated into the chip or can be separate from the chip, and in contact with the liquid sample. In the fluid reservoir is a sequencing reaction mixture that allows a single polymerase enzyme proximate to the nanoscale electrodes to perform nucleic acid synthesis. The sequencing reaction mixture has nucleotide analogs with redox labels that are cleaved when the nucleotide is incorporated into the growing nucleic acid strand. The enzyme is proximate to the nanoscale electrodes such that when a nucleotide analog is associated with the polymerase enzyme on its way to incorporation into the growing chain, the redox label on the nucleotide analog is repeatedly oxidized and reduced at the nanoscale electrode. The voltage/current source varies the voltages at the nanoscale electrodes over time, such that during some time periods, one redox label will undergo repeated oxidations and reductions, and during other time periods, a different label will undergo repeated oxidations and reductions. The current meter measures redox current flowing to and from the nanoscale electrodes. The measurement of redox current indicates the presence of a redox label held within the enzyme. A computer monitors the measured current over time at the current meter, and uses this information to determine the sequence of nucleotide incorporation. The repeated oxidation and reduction provides a signal which indicates that the nucleotide corresponding to that label is being incorporated into the growing strand. By measuring a time sequence of incorporation, the sequence of the growing strand, and thereby the sequence of the corresponding template nucleic acid is ascertained.

In some cases two nanoscale electrodes are used to perform nucleic acid sequencing by measuring the presence of the redox labeled nucleotide analog within the enzyme complex. FIG. 1 provides a schematic representation of a method for real time nucleic acid sequencing with two nanoscale electrodes and a polymerase-template complex bound proximate to the nanoscale electrodes. A substrate 100 has a region on its surface with two electrodes 102 and 106 separated on the order of nanometers. The separation can be from 1 nm to 100 nm, or from 2 nm to 20 nm Here, an insulating region 104 between the electrodes provides separation. Onto the insulating region 104 between the electrodes is attached a polymerase enzyme complex comprising a polymerase enzyme 110 and a nucleic acid template 130. The complex is attached to the insulation region 104 by an attachment moiety 120. As shown in FIG. 1, the polymerase enzyme is attached to the surface. In some cases, the template nucleic acid can be attached to the surface, either directly, or through hybridization with a primer attached to the surface. In the figure, the nanoscale electrodes are shown as disposed on a horizontal surface. In some cases, the electrodes are disposed vertically, e.g. as a stack of layers. A vertical construction can be useful for producing the required nanoscale insulating region 104 between the electrodes.

The substrate comprising the nanoscale electrodes is contacted with a fluid comprising a sequencing reaction mixture. The sequencing reaction mixture has the reagents required for carrying out polymerase mediated nucleic acid synthesis. The sequencing reaction mixture will generally include Mn++ or Mg++ salts for activating the enzyme, as well as other salts such as Na+ or K+ for providing the appropriate ionic strength. These salts also provide the solution conductivity required for electrochemical measurements at the electrodes. The type and amount of ions in solutions are adjusted for providing adequate solution conductivity for redox measurements. The sequencing reaction mixture also contains redox labeled nucleotide analogs such as labeled nucleotide analog 140. In FIG. 1, nucleotide analog 140 is a cognate nucleotide having a base that is complementary to the next position in the template nucleic acid 130. The nucleotide analog 140 has a nucleotide portion comprising a nucleobase, a sugar, and a polyphosphate portion 144. The nucleotide analog 140 has a redox label 142 that is attached to the polyphosphate portion of the nucleotide portion 144 through linker 146. The linker is selected such that when the nucleotide portion 144 associates with the polymerase enzyme as nucleotide analog 144 is incorporated, the redox label, 142 is able to diffuse close enough to both of the nanoscale electrodes 102 and 106 to allow for electron transfer for oxidation and reduction.

In FIG. 1(B) the nucleotide analog 140 is held in the active site of the polymerase enzyme 110. Because it is a cognate nucleotide, it is recognized by the enzyme as such, and will be held in the enzyme longer than will a non-cognate nucleotide. At the time that the nucleotide analog 140 is associated, the electrode 102 is at a potential that will oxidize the reduced form of redox label 142, and electrode 106 is at a potential that will reduce the oxidized form of the redox label 142. As the redox label is tethered to the surface proximate to the electrodes, the label is subject to repeated oxidations and reductions. In FIG. 1(C), the tethered redox label diffuses close enough to electrode 102 such that electron transfer from the redox label to the electrode (oxidation) occurs. In FIG. 1(D), the tethered oxidized label diffuses away from electrode 102. In FIG. 1(E) the oxidized form of the redox label diffuses near electrode 106 and electron transfer from the electrode to the oxidized form of the redox label occurs. While the nucleotide analog 142 is held within the enzyme, the cycle (B) (E) can happen many times. When the nucleotide analog 140 is incorporated into the growing strand as shown in FIG. 1(F), the polymerase enzyme cleaves the polyphosphate portion of the nucleotide analog. This cleavage occurs between the alpha and beta phosphates in the polyphosphate portion which releases the portion of the nucleotide analog comprising the label 142, which diffuses away from the substrate. This cleavage and diffusion away of the label ends the period of multiple oxidation and reduction cycles. Thus, the current due to the multiple oxidation and reduction events (C) and (E) begins when the nucleotide analog to be incorporated associates with the enzyme, and ends when the nucleotide is incorporated and the label diffuses away. This redox current, then, provides a measure of the residence time of the nucleotide analog in the active site of the polymerase prior before incorporation, which can be used to determine that a nucleotide incorporation event has occurred.

The paragraphs above describe the detection of one nucleotide analog. The same approach is applied to the measurement of the incorporation of more than one analog, for example 2, 3, 4, 5 or more analogs. For example, typically four different types nucleotide analogs corresponding to either A, G, C, T, for DNA or A, G, C, U for RNA are used. Each of the four types of nucleotide analogs has different and distinguishable redox characteristics, e.g. four different redox labels. The different types of nucleic acid analogs can have different redox potentials, different current amplitudes, or can have other distinguishable electrical characteristics such as different current oscillation color or can have combinations of the above.

Where two or more labels with different redox potentials are used, the voltage on the nanoscale electrodes can be varied with time to provide separate time periods during which only one of the redox labels will be repeatedly oxidized and reduced, or where one of the redox labels is repeatedly oxidized and reduced more effectively than the other labels. The periods of current flow indicating the incorporation of specific types of labels and therefore specific nucleotides can be used to determine a time sequence of incorporation of the different types of bases, thereby providing a measurement of the sequence of at least a portion of the template nucleic acid in the polymerase-template complex.

Figure 2:
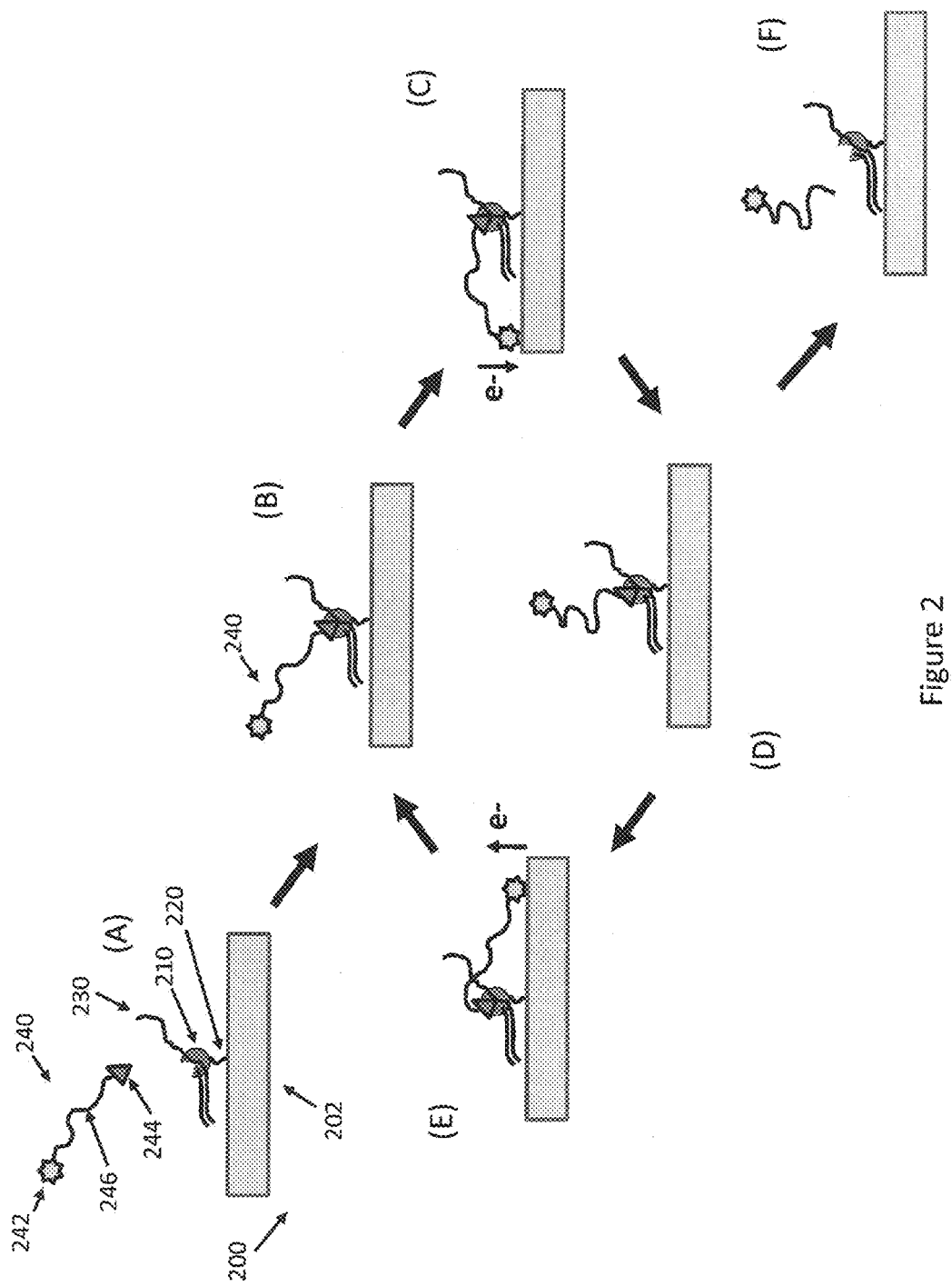
FIG. 2 shows an embodiment of the invention in which single molecule sequencing is carried out using a nanoscale redox device with a single nanoscale working electrode.

In some cases a single nanoscale electrode is used to perform nucleic acid sequencing by measuring the presence of the redox labeled nucleotide analog within the enzyme complex. FIG. 2 provides a schematic representation of a method for real time nucleic acid sequencing with one nanoscale electrode and a polymerase-template complex bound proximate to the nanoscale electrode. A substrate 200 has a region on its surface with nanoscale electrode 202. Onto the electrode 202 is attached a polymerase enzyme complex comprising a polymerase enzyme 210 and a nucleic acid template 230. The complex is attached to the electrode 202 by an attachment moiety 220. In some cases the polymerase is not attached to the electrode 202, but is attached to the substrate proximate to the electrode or to an insulating region on top of the electrode. The attachment must be close enough to the electrode that a redox label on a nucleotide analog in the active site can reach the electrode to be oxidized and reduced. As shown in FIG. 2, the polymerase enzyme is attached to the surface. In some cases, the template nucleic acid is attached to the surface, either directly, or through hybridization with a primer attached to the surface.

The substrate comprising the nanoscale electrode is contacted with a fluid comprising a sequencing reaction mixture. The sequencing reaction mixture has the reagents required for carrying out polymerase mediated nucleic acid synthesis. The sequencing reaction mixture will generally include Mn++ or Mg++ salts for activating the enzyme, as well as other salts such as Na+ or K+ for providing the appropriate ionic strength. These salts also provide the solution conductivity required for electrochemical measurements at the electrode. In some cases the type and amount of ions in solutions is adjusted for optimum solution conductivity. The sequencing reaction mixture also contains redox labeled nucleotide analogs such as labeled nucleotide analog 240. In FIG. 2, nucleotide analog 240 is a cognate nucleotide having a base that is complementary to the next position in the template nucleic acid 230. The nucleotide analog 240 has a nucleotide portion comprising a nucleobase, a sugar, and a polyphosphate portion 244. The nucleotide analog 240 has a redox label 242 that is attached to the polyphosphate portion of the nucleotide portion 244 through linker 246. The linker is selected such that when the nucleotide portion 244 associates with the polymerase enzyme as nucleotide analog 244 is incorporated, the redox label, 242 is able to diffuse close enough to both of the nanoscale electrode 202 for electron transfer for oxidation and reduction.

In FIG. 2(B) the nucleotide analog 240 is held in the active site of the polymerase enzyme 210. Because it is a cognate nucleotide, it is recognized by the enzyme as such, and will be held in the enzyme longer than will a non-cognate nucleotide. At the time that the nucleotide analog 240 is associated, the electrode 202 is being alternately held at different potentials having at least one potential that will oxidize the reduced form of redox label 242, and at least one potential that will reduce the oxidized form of the redox label 242. As the redox label is tethered to the surface proximate to the electrodes, the label is subject to repeated oxidations and reductions. In FIG. 2(C), the redox label diffuses close enough to electrode 202 at the appropriate time when electron transfer from the redox label to the electrode (oxidation) occurs. In FIG. 2(D), the oxidized label diffuses away from electrode 202. In FIG. 2(E) the oxidized form of the redox label diffuses near electrode 202 at a time during which electron transfer from the electrode to the oxidized form of the redox label occurs. While the nucleotide analog 240 is held within the enzyme, the cycle (B)-(E) can happen many times. Because diffusion is random, a reduction and oxidation cycle is not guaranteed to occur with every change of the potential of the electrode. In such cases, the label simply skips one cycle and the process can resume on the next cycle. Since there are many cycles per incorporation event, this small reduction in current does not interfere with detection of identification of the label. As shown in FIG. 2(F) when the nucleotide analog 240 is incorporated into the growing strand, the enzyme cleaves the polyphosphate portion of the nucleotide analog. This cleavage occurs between the alpha and beta phosphates, releasing the portion of the nucleotide analog comprising the label 242, which diffuses away from the substrate. The cleavage and diffusion away of the label ends the period of multiple oxidation and reduction cycles. Thus, the current due to the multiple oxidation and reduction events (C) and (E) begins when the nucleotide analog to be incorporated associates with the enzyme, and ends when the nucleotide is incorporated and the label diffuses away. This redox current, then, provides a measure of the residence time of the nucleotide analog in the active site prior before incorporation, which can be used to determine that a nucleotide incorporation has occurred.

The paragraphs above describe the detection of one nucleotide analog. The same approach can be applied to the measurement of the incorporation of more than one analog, for example 2, 3, 4, 5 or more analogs. For example, typically four different types nucleotide analogs corresponding to either A, G, C, T, for DNA or A, G, C, U for RNA are used. Each of the four types of nucleotide analogs has different and distinguishable redox characteristics, e.g. four different redox labels. The different types of nucleic acid analogs can have different redox potentials, different current amplitudes, or can have other distinguishable electrical characteristics such as different current oscillation color or can have combinations of the above.

Where two or more labels with different redox potentials are used, the voltage on the nanoscale electrode can be varied with time to provide separate time periods during which only one of the redox labels will be repeatedly oxidized and reduced, or where one of the redox labels is repeatedly oxidized and reduced more effectively than the other labels. The periods of current flow indicating the incorporation of specific types of labels and therefore specific nucleotides can be used to determine a time sequence of incorporation of the different types of bases, thereby providing a measurement of the sequence of at least a portion of the template nucleic acid in the polymerase-template complex.

Figure 3:
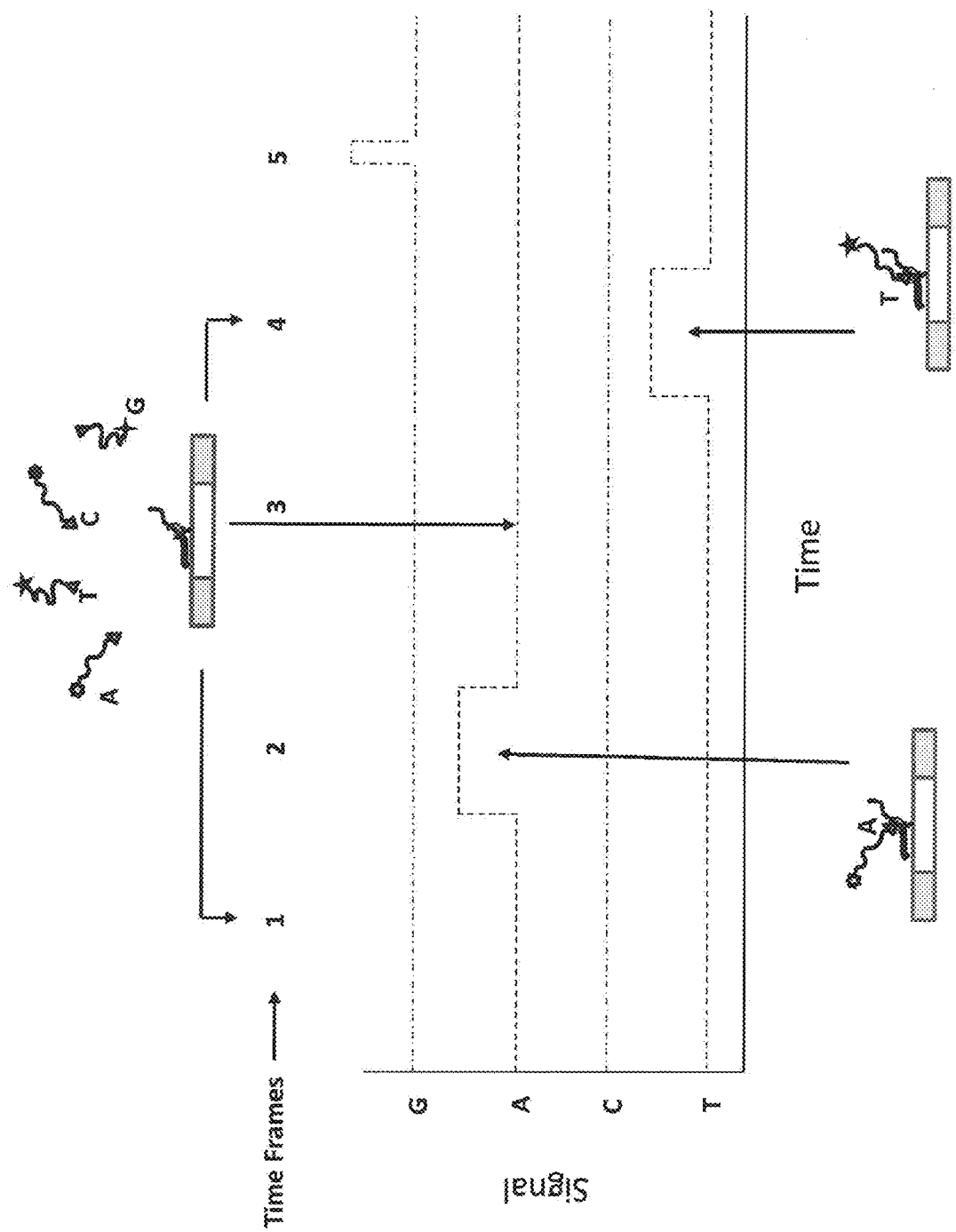
FIG. 3 illustrates the sequencing method, showing how current signals versus time can be used to identify incorporated nucleotide analogs.

FIG. 3 shows how the invention can be used to call a series of bases for sequencing. A graph is shown indicating the signal that is detected for each of four types of DNA analogs corresponding to bases G, A, C, and T. A two electrode system as described above is used where a polymerase-template complex is bound to an insulating region between the two nanoscale electrodes. The same approach described here can be used to sequence using the one electrode configuration. There are four types of nucleotide analogs, each having a different redox label, for example, each with a different redox potential. Throughout the time of the experiment, the voltage on each of the two electrodes is stepped to four voltage states. At each voltage state, the two electrodes are at potentials spaced apart such that repeated oxidation and reduction of one of the four labels happens preferentially (e.g. voltage state 1=A, voltage state 2=G, voltage state 3=C, voltage state 4=T). The time for the voltage to be taken through the four states is small compared to the time of a nucleotide binding event that corresponding to incorporation. Thus, the voltage is taken through the four states multiple times for a time period corresponding to incorporation.

The method is described in FIG. 3 by referring to 5 different time frames. During time frame 1, none of the four nucleic acid analogs is associated with the polymerase enzyme, and therefore none of the four voltage states detects an appreciable amount of current relating to repeated oxidation and reduction. In time frame 2, a nucleotide analog corresponding to nucleobase A is in the active site for a time that is characteristic of incorporation (e.g. 10 msec to 500 msec). During this time frame, repeated oxidation and reduction is seen during the time corresponding to voltage state 1 corresponding to A, but appreciable current is not measured in the time periods corresponding to the other types of nucleotide analog. This level of current for a residence time corresponding to incorporation indicates the incorporation of A. When the nucleotide is incorporated, the redox label is cleaved ending the current signal at voltage state 2. In time frame 3, again none of the four channels detects an appreciable amount of current relating to repeated oxidation and reduction indicating that no nucleotide analog is in the active site of the polymerase. During time frame 4, a nucleotide analog corresponding to T is incorporated and is held within the active site for a characteristic period of time. During the time frame repeated oxidations are seen during the time corresponding to voltage state 4, indicating the presence of T. When the analog is incorporated, the label is cleaved, and diffuses away ending the measurement of current at voltage state 4. In time frame 5 for a short time, repeated oxidation of a redox label corresponding to G is detected. The time that the G is present near the electrode is too short to be associated with an incorporation event. This type of feature is seen, for example where a non-cognate nucleotide is sampling the active site, after which it diffuses from the enzyme. During the time of the portion of the experiment shown in FIG. 3, the data indicate that an A and a T were incorporated, which thus indicates that there is a T and an A in the complementary sequence of the template. While this description relates to the incorporation of two nucleotides, this method can be used to sequence long stretches of nucleic acids from hundreds to tens of thousands of bases or more.

The example of FIG. 3 is carried out with four nucleotides, each having a redox label with a different reduction potential. It will be understood that the same approach described in FIG. 3 can be applied to cases in which current amplitude or current oscillation color or any combination of the three is used to identify the incorporated bases. Note, for example, that the number of voltage states required will depend on the number of labels having different redox potentials. For example, four nucleotides can be used having: a nucleotide corresponding to A having a label with redox moiety A with linker 1, a nucleotide corresponding to G with redox moiety 1 and linker 2, a nucleotide corresponding to T with linker 1 and redox moiety 2, and a nucleotide corresponding to C with redox moiety 1 and linker 2; where linker 1 exhibits a different of current oscillation color than linker 2, and redox label one has a reduction potential that is different than redox label 2. Here, only two voltage states will be required, but the distinction between A and G and between T and C is made on the basis of current oscillation color.

In some cases, particularly for the one electrode configuration, redox cycling can be obtained by having a reduction or oxidation reagent in solution. For this embodiment, the single working nanoscale electrode is, for example, biased to only perform reduction such that oxidation is carried out by a oxidizing species in solution. Alternatively, the nanoscale electrode is biased to perform oxidation of the redox label, and a reducing species in solution performs reduction in solution. In this manner, the signal amplification advantages of redox cycling can be employed for sequencing using a one electrode system. The oxidation or reduction species in solution should not react directly with the electrode, or should react very slowly with the electrode in order to minimize unwanted current signal from. Solution redox species include hydrazine and NADH. See for example: Das et al. Anal Chem. 79, 2790, 2007; Kwon et al. Analyst, 133, 1599, 2008; Osyczka et al. Nature, 427, 607, 2004; and Goldsmith et al. PNAS, 108(42), 17269, 2011 which are incorporated herein by reference for all purposes.

In some aspects, the invention provides a method of sequencing a template nucleic acid comprising: disposing a polymerase enzyme complex comprising a polymerase enzyme, a template, and a primer proximate to a working electrode; exposing the polymerase to a solution comprising the components required for carrying out polymerase mediated nucleic acid synthesis, the solution including a plurality of nucleotide analogs, each nucleotide analog having a different redox label, each redox label attached to the phosphate portion of the nucleotide analog so as to be cleaved and released upon incorporation of the nucleotide analog into a growing nucleic acid strand; measuring an electrical signal from a redox measuring system comprising the working electrode, optionally a counter electrode, and optionally a reference electrode to determine the presence and identity of a nucleotide analog in the active site of an enzyme by its redox label; and monitoring the electrical signal over time to determine a sequence of the template nucleic acid.

Arrays of Nanoscale Electrode Redox Devices

Some aspects of the invention provide arrays of devices for carrying out real time redox sequencing. The arrays of devices comprise chips having multiple nanoscale electrode redox regions, each in either the one electrode or the two electrode configuration described herein. In referring to a one electrode or a two electrode configuration, we refer to a chip having one or two working electrodes, which are the electrodes at which electrochemistry of the redox labels is carried out and measured. In some cases the chips comprising arrays of devices will also comprise either a counter electrode or array of counter electrodes, an array of reference electrodes or a reference electrode. In some cases, the chips will have both counter and reference electrodes or will have arrays of both reference and counter electrodes.

The chips of the invention can be produced using known semiconductor processing techniques. These techniques allow for inexpensively producing arrays having large numbers of redox devices. The chips have, for example, from 2 to one million or more redox devices. In some cases the chips have 9 to 100, 100 to 10,000, or from 10,000 to one million or from 100,000 to 10 million redox devices. The number of devices on a chip will depend on the type of application that for which the chip is used. In some cases, having less than 100 redox devices is useful, for example in diagnostic applications where a specific answer may be desired in a short time frame. For applications in which high throughput is desired, for example whole human genome sequencing, then having a million to 10 million devices is used. It is understood by those of skill in the art that as the number of redox devices grows, there are more demands on the system in which the chip is used such as more complex drive and sensing electronics and higher throughput data analysis. Current high throughput sequencing techniques have shown that these issues can be addressed with the appropriate level of engineering.

In some cases, the chips have nanoscale redox devices comprising one or two working electrodes, and electric interconnects connecting the redox devices to electrical outputs on the chip. In addition, in some cases there is a counter electrode on the chip for each redox device. In some cases there is one counter electrode on the chip for multiple redox devices on the chip. For example there can be one counter electrode on the chip for each 1 to each 1,000 devices, one counter electrode for each 10 to 100 devices, or one counter electrode on the chip for all of the devices on the chip.

Typically, where a reference electrode is used, the reference electrode will be separate from the chip, but in some cases, the reference electrode can be on the chip. As with the counter electrodes, in some cases there is a reference electrode on the chip for each redox device. In some cases there is one reference electrode on the chip for multiple redox devices on the chip. For example there can be one reference electrode on the chip for each 1 to each 1,000 devices, one reference electrode for each 10 to 100 devices, or one reference electrode on the chip for all of the devices on the chip.

The chips can also have corresponding arrays of control electrodes. A control electrode is used to improve signal to noise by having similar characteristics to the working electrode, but not having a polymerase enzyme bound proximate to it. Subtracting the signal at the control electrode from the signal at the working electrode can remove noise that is common to both electrodes, and thus improve the signal to noise ratio of at the working electrode. In some cases there is a control electrode on the chip for each redox device. In some cases there is one control electrode on the chip for multiple redox devices on the chip. For example there can be one control electrode on the chip for each 1 to each 1,000 devices, one control electrode for each 10 to 100 devices, or one control electrode on the chip for all of the devices on the chip. In some cases, the control electrode can constitute a control redox device, for example a control two electrode redox device that intentionally does not have a polymerase enzyme bound proximate to the electrodes.

The chips can also have other components incorporated into the chip. Since the devices are made by semiconductor processing techniques, it is straightforward to include other components such as resistors, capacitors, amplifiers, memory circuits, A/D converters, logic circuits, and the like. The circuits can provide the functions of amplification, analog to digital conversion, signal processing, memory, and data output. By having components such as CMOS processors included in the device addresses the issue of monitoring multiple events simultaneously. Rather than having at least one pair of wires bringing signals out from the chip, the inclusion of these components allows for a multiplexed output or an addressable output such as used in a DRAM chip. Where the number of devices is large, there tends to be more of a demand for building in extra circuitry onto the chip. This allows for carrying out partial analysis on the chip in a way that can significantly reduce the need for the amount of electrical signals that have to go to and from the chip.

The electrodes can be made of any suitable conducting material. They are typically made of a conductive metal that is amenable to semiconductor processing. Metals include silver, gold, platinum. The electrodes are fabricated to be on the order of nanometers in size. The size of the electrode is dependent on various design parameters. When discussing the size of the electrodes in this application, we are generally referring to the portion of the electrode which is exposed to the fluid sequencing mixture. In many cases, the size of the conductive portions not in contact with the solution are made larger in size to increase conduction. The electrode should be large enough that when a nucleotide analog having a redox label is in the active site, the redox label will efficiently contact the electrode. If the electrode is has a size that extends well beyond the reach of the redox label, that portion of the electrode will not be effective at measuring signal, but can measure noise (e.g. freely diffusing labels). The best size of the electrode is not a fixed number and will depend, for example, on the length of the linker in the oligonucleotide. A longer oligonucleotide linker will tend to allow the redox label on a nucleotide analog in the active site to sample a larger volume and therefore a larger area on the substrate.

Figure 4:
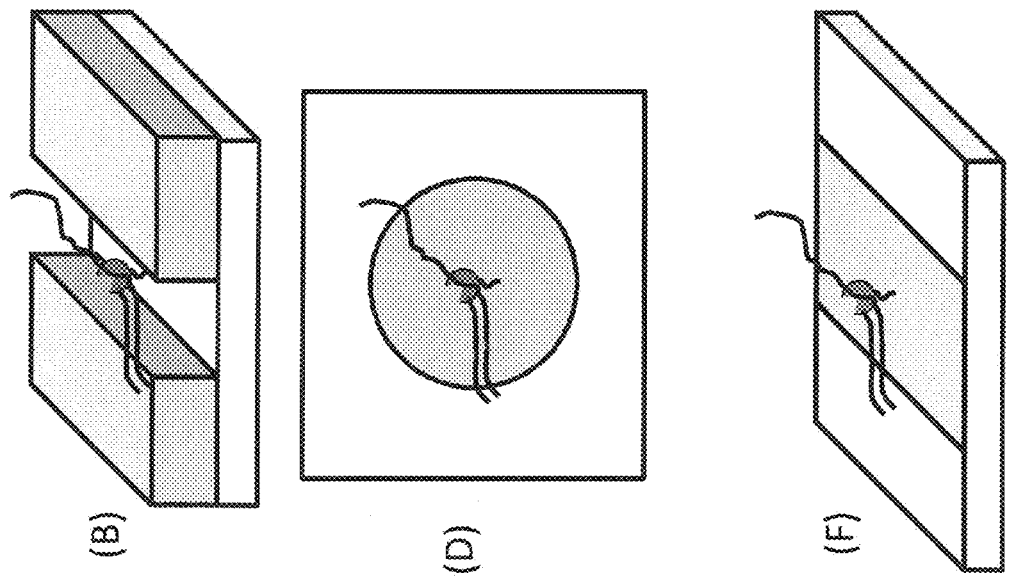
FIGS. 4(A), 4(B), and 4(C) each show embodiments for two electrode configurations of redox devices.
FIGS. 4(D), 4(E), and 4(F) show some embodiments for one electrode configurations of redox devices.
Figure 4:
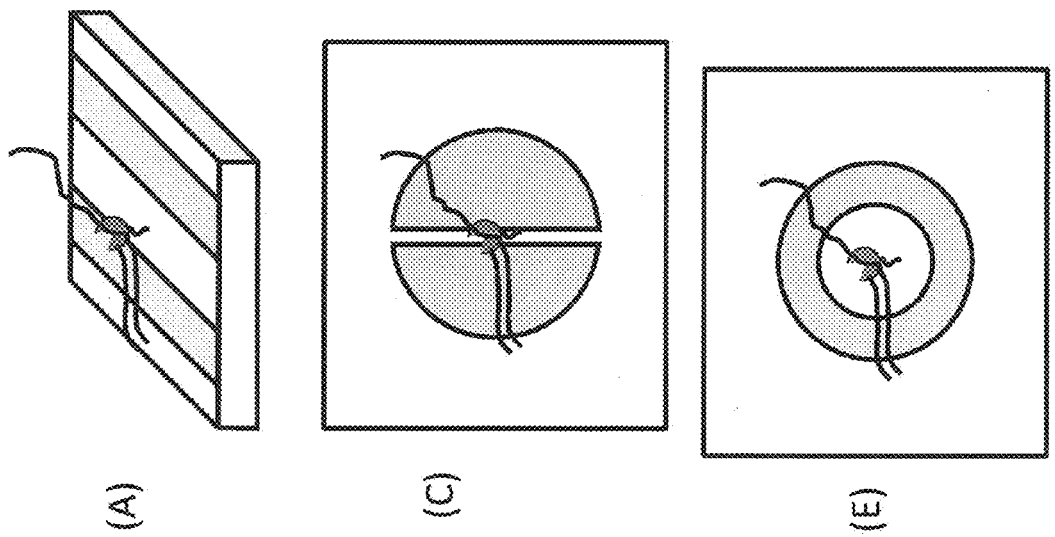

FIG. 4 shows some approaches to the geometry of the electrodes of the invention. FIG. 4(A) shows a two electrode configuration with linear electrodes on an insulating substrate. FIG. 4(B) shows a two electrode configuration where the enzyme is attached to an insulating layer between walls of electrode. In this configuration, the redox labeled nucleotide analog does not have to extend all the way to a flat surface, but can come into contact with the sidewalls. Note that for (B), the electrode can be made such that only the inside walls of the electrode are effective for conducting electrons for redox reactions. FIG. 4(C) shows a split circular electrode with an insulating strip in the middle to which the enzyme is attached. In some cases, a circular profile such as this can be used to maximize the amount of electrode that is available to the redox label while not having electrode area that is not likely to be visited by the redox label. FIG. 4(D) shows a circularly symmetric single electrode configuration where the enzyme complex is attached to the electrode. Figure (E) shows a circularly symmetric single electrode configuration in which the enzyme complex is attached to a middle insulating region. This configuration can be useful for providing a chemically distinct region to facilitate selective binding of the polymerase complex. FIG. 4(F) shows a single electrode linear electrode configuration on a flat insulating surface. The electrodes can have any suitable geometry.

Figure 5:
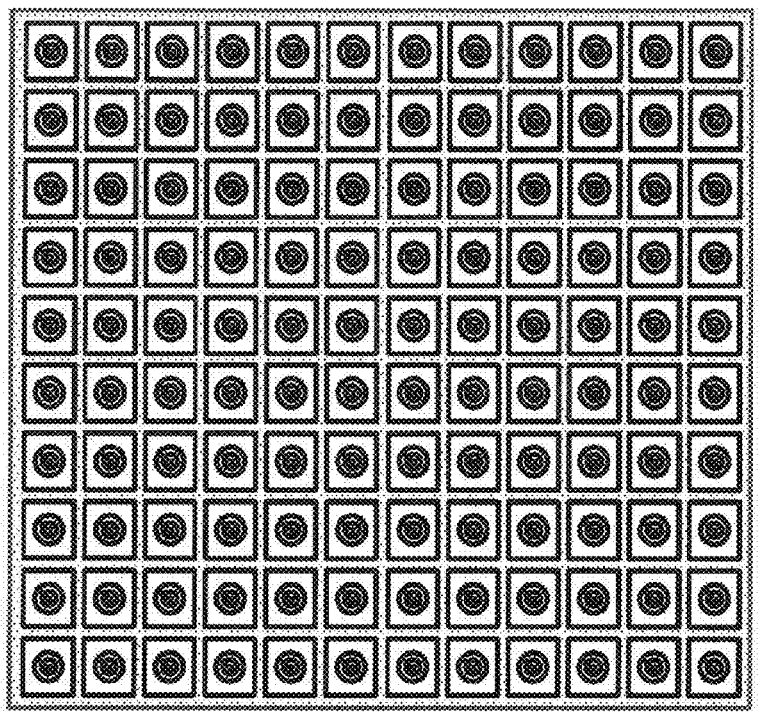
FIG. 5(A) illustrates how arrays of nanoscale devices, each having two working electrodes, on a chip can be fabricated to allow for simultaneously sequencing multiple templates.
FIG. 5(B) illustrates how arrays of nanoscale devices, each having one working electrode on a chip can be fabricated to allow for simultaneously sequencing multiple templates.
Figure 5:
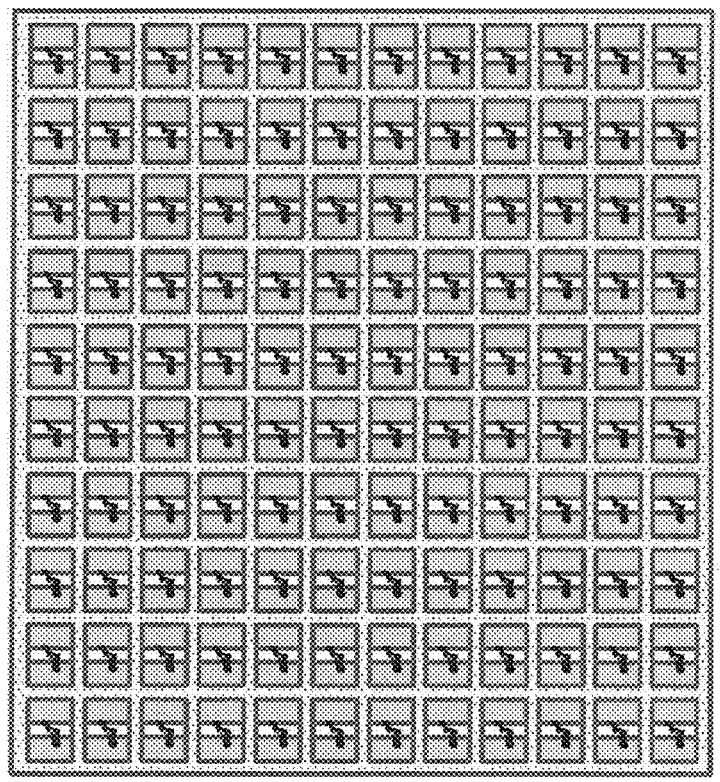

FIG. 5 (A) illustrates an array of a linear two electrode configuration redox devices. A semiconductor surface can be patterned to produce an array of redox devices. The interconnects to connect the nanoscale electrodes to the electrical inputs and outputs can be provided by dropping through vias to lower layers. The electrical connections to the chip are typically made to the sides or to the bottom of the chip. FIG. 5(B) illustrates an array of circularly symmetric one electrode configuration redox devices.

Figure 6:
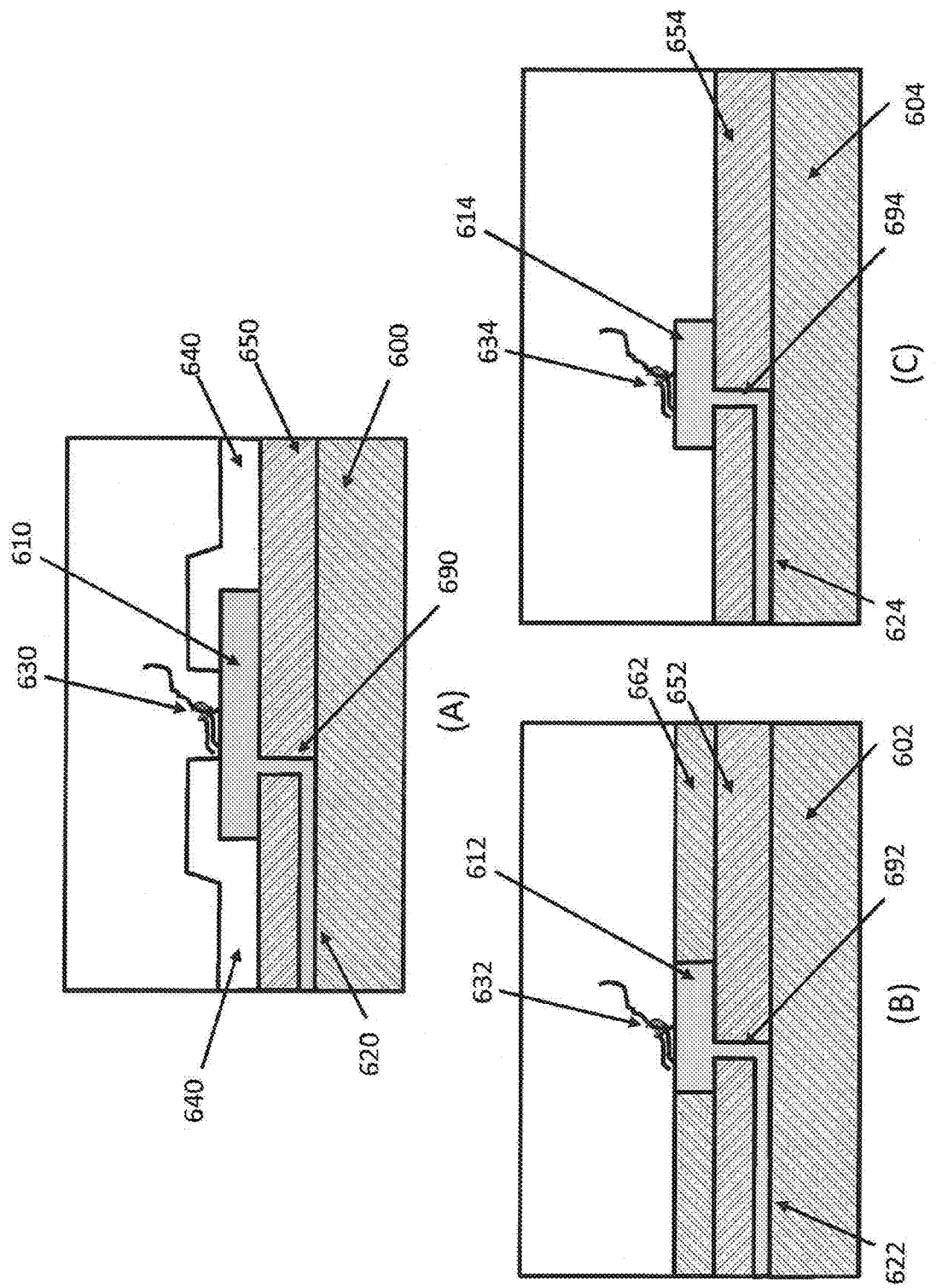
FIG. 6(A) shows a structure for forming a single electrode redox device of the invention.
FIG. 6(B) shows an alternative structure for forming a single electrode redox device of the invention.
FIG. 6(C) shows another alternative structure for forming a single electrode redox device of the invention.

FIG. 6 shows some exemplary approaches to single electrode configuration redox devices using standard semiconductor processes. These constitute relatively straightforward semiconductor device structures which are made as arrays on chips by standard semiconductor manufacturing techniques. In FIG. 6(A) a substrate 600, typically silicon, has electrical trace 620 extending across the substrate 600. The interconnect 620 and connects with the electrode 610 through via 690 which extends through layer 650. Insulating layer 640 is deposited on top of the electrode 610 to create a well of insulating material. The enzyme complex 630 is bound to the top of the electrode within the insulating well. In FIG. 6(B) electrical interconnect 622 extends across substrate 602, and via 692 extends through layer 652 to electrode 612. A planarization layer 662 is deposited and optionally polished in order to produce the electrode configuration flush with the surface to which the enzyme complex 632 is attached. In FIG. 6(C) electrical interconnect 624 extends across the substrate 604. Via 694 extends through layer 654 and connects the electrical interconnect 624 to the electrode 614. The polymerase-template complex 634 is attached to electrode 614.

Figure 7:
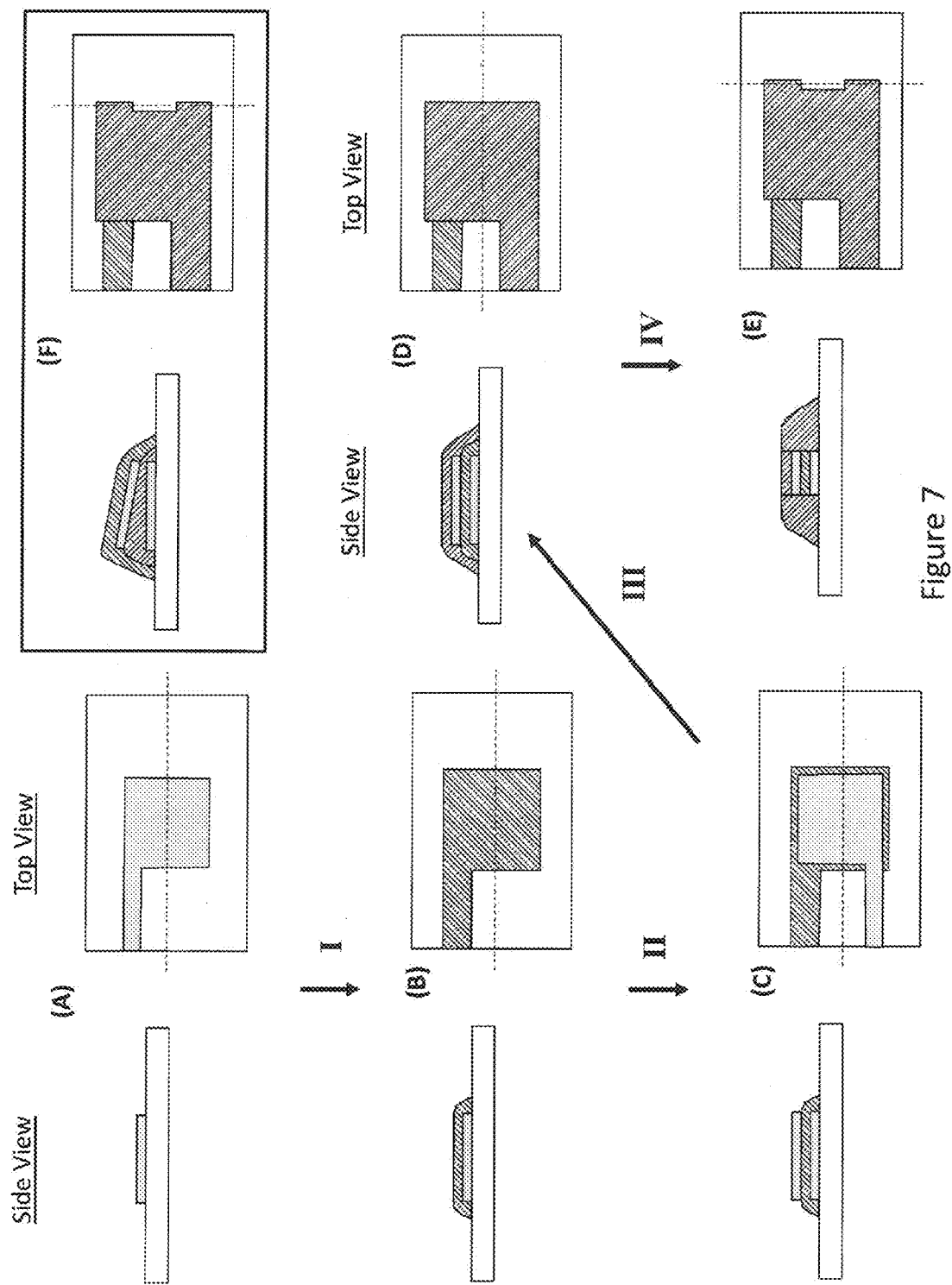
FIG. 7 shows an exemplary process for producing a two electrode redox device of the invention.

For the two electrode configuration, the two electrodes can be disposed, for example, horizontally or vertically with respect to the top of a substrate. A vertical configuration can be useful for producing thin layers, e.g. from 1 nm to about 100 nm, 2 nm and 50 nm, or 10 nm and 100 nm for the insulating layer between the two nanoscale electrodes. FIG. 7 shows an exemplary approach for producing an array of two electrode redox devices on semiconductor substrates. In each of FIGS. 7(A) thorough (F) both a top view and a side view of the device is shown. FIG. 7(A) shows a patterned metal electrode on a substrate such as a silicon substrate. The pattern creates the lower electrode pad and a interconnect that can run out for creating a electrical connection to the chip. In step I, an insulating layer, e.g. $SiO_2$ is deposited, patterned, and etched such that the bottom electrode is covered (FIG. 7(B)). This layer will become the insulating layer between the two nanoscale electrodes in the redox device. The insulating layer is typically deposited at a thickness of between 2 nm and 20 nm. While the insulating layer in FIG. 7 is shown as being flat, in some cases, the insulating layer is deposited with decreasing thickness toward the edge that is eventually exposed to form the electrode device. The variation in thickness can allow for having a thin, e.g. 1-10 nm layer where the $SiO_2$ layer is exposed, but having a thicker layer in other portions of the device in order to keep the capacitance low. In step II, the top electrode layer is deposited on top of the insulating layer, with the electrode extending off to produce an electrical interconnect (FIG. 7(C)). In step III, a second insulating layer is deposited over the top electrode layer. The second insulating layer is typically different from the first insulating layer, and can be for example silicon nitride or aluminum oxide. Having the first insulating layer (e.g. $SiO_2$) made of a different material can be useful for selectively binding enzyme to the layer between the electrodes (FIG. 7(D)). In step IV, a notch is etched into the electrode insulator stack to expose a portion of the top and bottom electrode and insulating layer (FIG. 7(E)). FIG. 7(F) shows an alternative to the final device in which the electrode layers are angled with respect to one another. This angling allows for the portions of the electrodes that are exposed to be close together (i.e. the $SiO_2$ layer between the electrodes is thin), and it also allows for the bulk of the electrodes to be farther apart from one another, which lowers the capacitance of the redox device, allowing for faster charge up and charge down. This method allows for a small and well-controlled two-electrode redox device.

Distinguishing Labels—Calling Bases

In the sequencing methods of the invention, there are usually two or more different types of labeled nucleotide analogs, and typically there are four different types of nucleotide analog. There are various approaches to distinguish the various types of bases. The discussion will generally involve distinguishing four bases but it is understood that the same approaches can be used to distinguish, two, three, five or more types of nucleotide analogs.

Distinguishing nucleotide types is done, for example, using the characteristics of redox potential, amplitude, and current versus time characteristics (current oscillation color). Combinations of the above can also be useful; for example by using two labels and two amplitudes; two redox potentials and two types of current oscillation color, etc.

Redox labels having a wide variety of redox potentials are well known in the art, allowing for the selection of, for example, 2, 3, 4, or 5 labels having different redox potentials for use in a sequencing system of the invention. Acceptable redox labels can comprise organic compounds, nanoparticles, metals, or other suitable substituent. The redox label should be readily oxidized and reduced repeatedly without degradation. The polymerization is typically carried out in an aqueous environment, so the nucleotide analog comprising the redox label should generally be soluble in water. In some cases, charged and polar substituents are present on the redox label to enhance water solubility. Such substituents include carboxylate, sulfate, sultanate, phosphate, phosphonate, ether, and ester substituents. Where suitable labels are described it is understood that such labels could also include solubilizing substituents. Suitable labels include substituted or unsubstituted 1,4-dihydroquinone, 1,4-dihydroxy-2-naphthoic acid, ferrocene, 2,5-dichloro-1,4-benzoquinone, Methylene Blue, Methyl-1,4-benzoquinone, anthraquinone, and nanoparticles such as CdS and ZnS nanoparticles. Suitable labels are described, for example in Levine et al., Biosensors and Bioelectronics, 24, 1995, 2000; Wang et al. J. Am. Chem. Soc. 125, 3214, 2003; and Kang et al. NPG Asia Materials, doi: 10.1038/am2012.1, which are incorporated herein by reference for all purposes.

Differentiating nucleotide analogs based on amplitude can be carried out, for example, by providing a redox label having multiple redox moieties on a nucleotide analog. In some cases 2, 3, 4, 5, 6, 7, 8, 9, 10, 11, or 12 redox moieties comprise the redox label on a nucleotide analog. In some cases, the redox label has 2 to 100 redox moieties. In some cases the redox label has 2 to 30 redox moieties. The nucleotide can, in some cases have more than one type of redox moiety. Multiple redox moieties can be included on a nucleotide analog using multivalent scaffolds or dendritic molecules. Generally in this application, each redox labeled nucleotide analog is described as having a redox label, and each redox label can comprise multiple redox moieties. It is to be understood that any redox label described herein can also be a redox moiety. In some cases, nucleotide analogs having multiple redox labels are referred to. Where this causes uncertainty, the nucleotide analog with multiple labels should be read as a nucleotide analog having multiple redox moities. Nucleotide analog structures including those having multivalent scaffolds and nucleotides having multiple moieties can be prepared as described, for example, in US Patent Application 20120058473 Molecular Adaptors for Dye Conjugates, and US Patent Application 20120077189 Scaffold-Based Polymerase Enzyme Substrates, which are incorporated herein by reference for all purposes. While these references generally describe a fluorescent label, it is to be understood in conjunction with the teachings of this application that a suitable redox label connected by a suitable linker as described herein can be substituted for the fluorescent label.

Nucleotide analogs can also be differentiated by the current versus time characteristics during repeated oxidation and reduction. The current versus time characteristics can be referred to as current oscillation color. For example, two nucleotide analogs, each having the same redox label but having different length linkers can exhibit different redox current versus time characteristics. The nucleotide with the longer linker, may, for example, diffuse through a larger volume, and thus contact the electrode or electrodes at a lower frequency than the nucleotide analog with the shorter linker. This difference in frequency of current oscillation can be used to determine which of the nucleotide analogs is associated with the enzyme. In addition to linker length, the current oscillation color can be influenced by other characteristics of the linker such as its spring constant. The current oscillation color will depend on the characteristics of the measurement system such as electrode geometry and polymerase complex attachment. These factors can be chosen to control differences in current oscillation color to enhance the determination of which nucleotide is incorporated.

For characterizing a redox label tethered to the surface through the nucleotide analog, polymerase and attachment moiety can, in some cases, be modeled as a diffusing species which diffuses within the volume that is accessible to it. As such, the redox label can oscillate due to Brownian motion to an electrode, away from an electrode, and back to an electrode again, leading to fluctuations in the redox current. This oscillation is manifested as a variation of the current over time. This variation can produce a magnitude and frequency spectrum which can be adjusted, for example, by choice of linker spring constant and length of the tether, including the linker, and by the diffusion characteristics of the label, allowing for identification of the nucleotide that has a characteristic current oscillation.

Nucleotides or analogs that can thus be identified by the spectrum of the electrical oscillation they produce. In some cases, oscillations looks like noise, but with reproducible and identifiable characteristics including the frequency and the magnitude of the signal. These different types of oscillations can be used like different colored dyes are used to differentiate between different nucleotide analogs in optical systems, thus, we refer herein to a distinguishable type of current oscillation as a current oscillation color.

While the measurement of redox current is described as a measurement of current, it is understood by those in the art that this current can in some cases be measured by measuring a voltage. Where we refer to measuring current or voltage, it is to be understood that one can be used to measure or represent the other with respect to measuring electron flow due to oxidation and reduction reactions. In addition to current and voltage, resistance or impedance measurements can also be employed.

One aspect of the invention is the utilization of additional parameters beyond just the amplitude and redox potential of a label to classify the species associated with the enzyme. Such parameters are measurable over the duration of a pulse. Two general categories of measurement scenarios are: quasi-equilibrium measurement and non-equilibrium measurement.

In quasi-equilibrium measurement, there is some static constraint that remains in place over the duration of the event, and that the removal of that constraint effectively determines the end of the event (except for a negligibly short interval at the end while the detectable object clears the electrode). Though the constraint is fixed, the rest of the components of the system are free to move, and this leads to fluctuations in the signal. For example, diffusion (or equivalently Brownian motion) will cause movement of the label. Under most circumstances, that motion will be correlated with changes in the current across the nanopore, and thus the voltages that might be measured elsewhere in the system. Because of this, aspects of the detectable moiety such as the submolecular diffusion constant (the diffusibility of just that part of the molecule, even when another part of the molecule is constrained) will change the speed of those motions and thus the characteristic frequencies with which the observed voltages or currents will change. For example, a fast diffuser will generally have a whiter noise spectrum, while a slower diffuser will tend to produce a pinker current oscillation spectrum.

The current oscillation color can be used as the basis for a discriminator, for example, by 1) taking the current oscillation signature over a region of interest (e.g. over the duration of the event), 2) performing a Fourier transform analysis or an autocorrelation analysis, and examine the spectrum of the current oscillation over the range of frequencies available (e.g. from $f=1/T$ where T is the duration of the pulse, up to the cutoff frequency of the amplifier system, or somewhat beyond the cutoff). This process will result in a digitally sampled current oscillation amplitude as a function of frequency. This could be represented by as few as two samples (a low frequency region and a high frequency region), 3, 4, 5, 6, 7, 8, 9, 10, 11, 12, 16, 32, 64, 128, 256, 512, 1024 or more bins. The values in these bins could be discrete samples of a function or they represent integrals over a region of interest of the idealized continuous function. This set of discrete values can be represented as a vector that can be classified by one of many machine learning systems such as k-means clustering, SVM, CART or boosted CART, PCA and many others. Thus, as described herein, current oscillation color can be used to discriminate detectable moieties. Detection systems that are based on current oscillation color can be referred to as "current oscillation color identification systems", and when moieties engineered for producing different current oscillation color are used, they are referred to as "current oscillation color tags". In a sequencing system, when nucleotide base sequence is identified on this basis it can be referred to as a current oscillation color sequencing system (whether the current oscillation color is intrinsic to the bases or the result of current oscillation color tags).

Other aspects besides the diffusion constant can affect the current oscillation color of the signal. For example, in the embodiments that use linkers with different elastic constants, this will affect the magnitude of these diffusive fluctuations, which will then affect the current oscillation signal (not to be confused with the amplitude of the DC current during the event—this is referring to the RMS noise of the signal over the duration of the event). In analogy with color systems that have RGB, or HSV, color can be generalized to include the "brightness" of the color. In the above-mentioned spectrum analysis model, this would result in the values in the vector being larger for moieties capable of larger excursions, and lower values for moieties that are more constrained in position. Some or all of these signals can be exploited in the machine learning paradigm indicated above. There are many aspects that can affect the size of the excursions.

Figure 8:
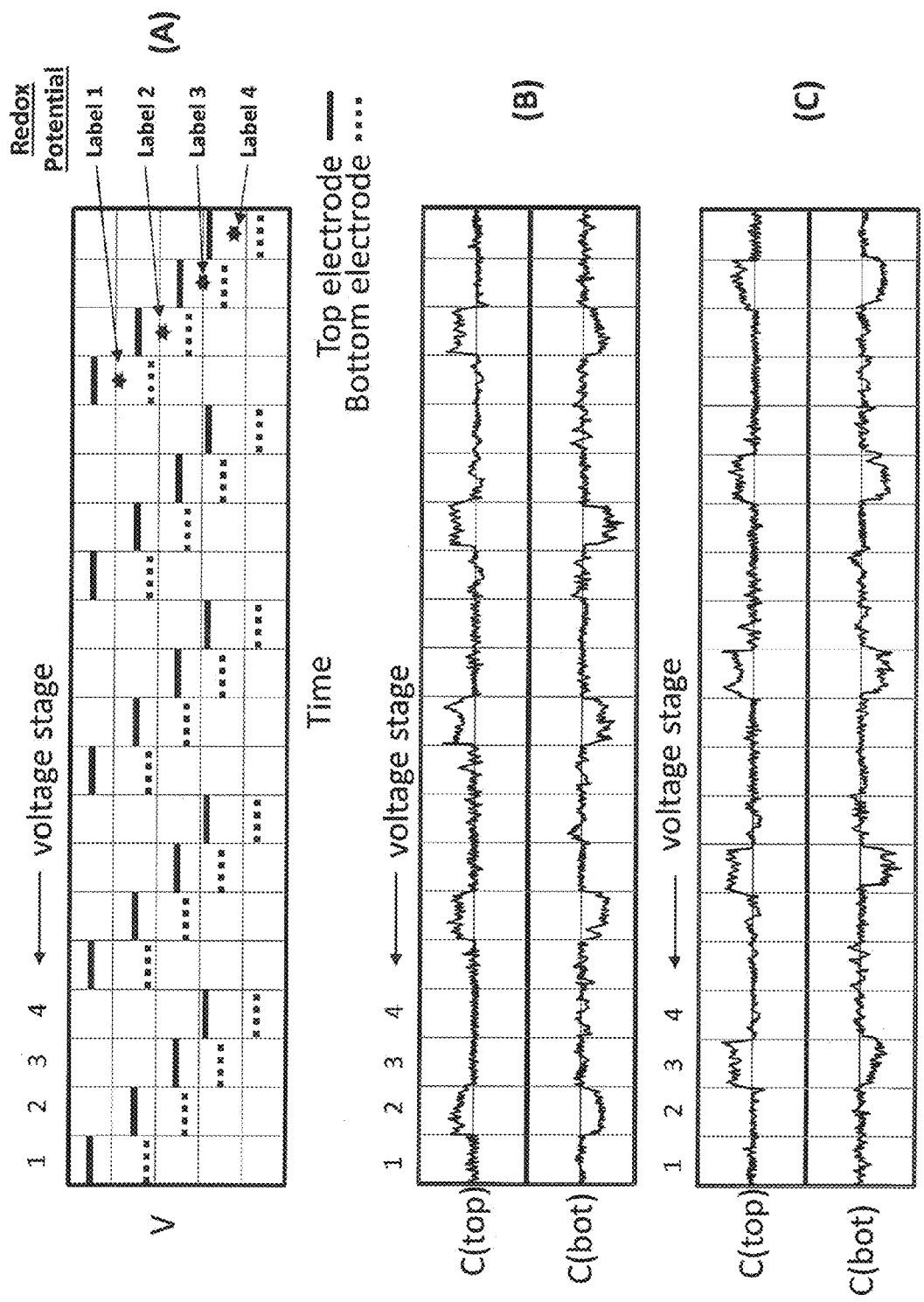
FIG. 8(A) shows exemplary voltages versus time applied to a two electrode configuration redox device.
FIG. 8(B) shows the resulting current signal for a nucleotide having redox label 2.
FIG. 8(C) shows the resulting current signal for a nucleotide having redox label 3.

FIG. 8 shows an example of how sequencing can be performed on a two electrode configuration using four nucleotide analogs, each having a different redox label that has a different redox potential. A sequencing system is set up as described herein. FIG. 8(A) shows a plot of the applied voltage on the top electrode (solid line) and bottom electrode (dashed line) versus time. There are four separate voltage states that are repeated. During each voltage state, the top electrode and bottom electrode is held at a voltage until the transition to the next voltage stage. FIG. 8(A) shows the redox potential of each of the four labels. The redox potentials of the labels are indicated on the figure with a (*). In each case the redox potential falls between the voltage of the top electrode and the voltage of the bottom electrode for a given voltage stage. This allows that label to be repeatedly oxidized and reduced during that voltage stage. For example, during voltage stage 1, redox label 1, if associated with the enzyme will be repeatedly reduced and oxidized. The other three redox labels do not have redox potentials between that of the top and bottom electrode, and therefore, these three labels will not be repeatedly oxidized and reduced during voltage stage 1 even if the nucleotide analog they are part of is in the active site of an enzyme. At each voltage stage, current due to repeated oxidation and reduction is indicative of the presence of the label proximate to the electrodes.

The labels shown in this example each nucleotide analog has a redox label with a redox potential that falls within the voltage of the upper electrode and the lower electrode at the voltage state corresponding to that nucleotide analog, and the redox potential falls outside of the range of the voltage of the upper electrode and lower electrodes in voltage states corresponding to the other three redox labels. This does not have to be the ease. For example, in some cases, the redox potential of a label will fall within the range voltage between the upper electrode and lower electrode where the voltage state is meant to detect a different redox label. Where this is done, it is typically done such that while the non-selected redox label is within the voltage range of the upper and lower electrodes, it is at a position within that range with is less effective at redox cycling than for the label that is selected. For example, the label that is selected can have a redox potential toward the middle of the voltage range, while the non-selected label can have a redox potential close to the upper or lower voltage. While this approach may lead to slightly more signal from the non-selected label, which is generally undesirable, the approach can result in an increase in the overall signal which can result in an improvement in the overall sequencing performance.

The timing of the stepping through the voltage stages is selected such that multiple stepping cycles are performed during an incorporation event. For example, the steps can each be 250 microseconds, such that a cycle of four steps happens once each millisecond. If the enzyme is selected such that on average, an incorporation event occurs over 200 milliseconds, then many stepping cycles will occur for each incorporation event, allowing for distinguishing an incorporation event from a shorter event such as non-cognate sampling or freely diffusing redox labels. The described timing is exemplary, other times may be used, but in general, the time for stepping through the voltage stages is less than the average (or median) time for incorporation. In some cases the time for cycling through the voltage stages is more than 10 times less than the average (or median) time for incorporation. In some cases the time for cycling through the voltage stages is more than 100 times less than the average (or median) time for incorporation. In some cases the time for cycling through the voltage stages is more than 1000 times less than the average (or median) time for incorporation.

FIG. 8(B) shows current traces for the situation where a nucleotide analog having redox label 2 is in the active site of the enzyme. During voltage stages 1, 3, and 4 no current above baseline is detected, but in voltage stage 2, current is measured in both the top and the bottom electrode. This figure highlights an advantage of the sequencing method of the invention. A redox cycling event involving repeated oxidations and reductions will result in current flow in both the bottom and the top electrode in that timeframe. This allows for higher confidence in the signal that is detected and a greater ability to distinguish signal from noise. In addition, in a redox cycling event, the current flow from the top electrode will be opposite in direction from the current flow in the bottom electrode, because oxidation happens at one electrode and reduction at the other. This feature also increases the ability to distinguish true signal from noise. During the time frame shown in FIG. 8(B), the voltage stages are stepped through 5 times. Through each cycle of voltage steps the presence of label 2 proximate to the electrodes is confirmed, indicating the presence of the nucleotide analog having label 2 in the active site of the enzyme. FIG. 8(C) shows a similar current trace to that in FIG. 8(C), but where a nucleotide analog having redox label 3 is within the active site of the enzyme. Here, throughout the 5 cycles of stepping through the voltage steps, current at both electrodes is measured only during voltage step 3, and not during the other three voltage steps. In this example, four labels, each with a different redox potential, are used. For this ease, only the presence of the label proximate to the electrode must be detected. As described herein, in some cases, current amplitude or current oscillation color, either separately or combined with other methods, are used. Where current amplitude or current oscillation color are used, the characteristics of the current as it is measured at a given voltage stage is quantified and used for calling an incorporated base.

Figure 9:
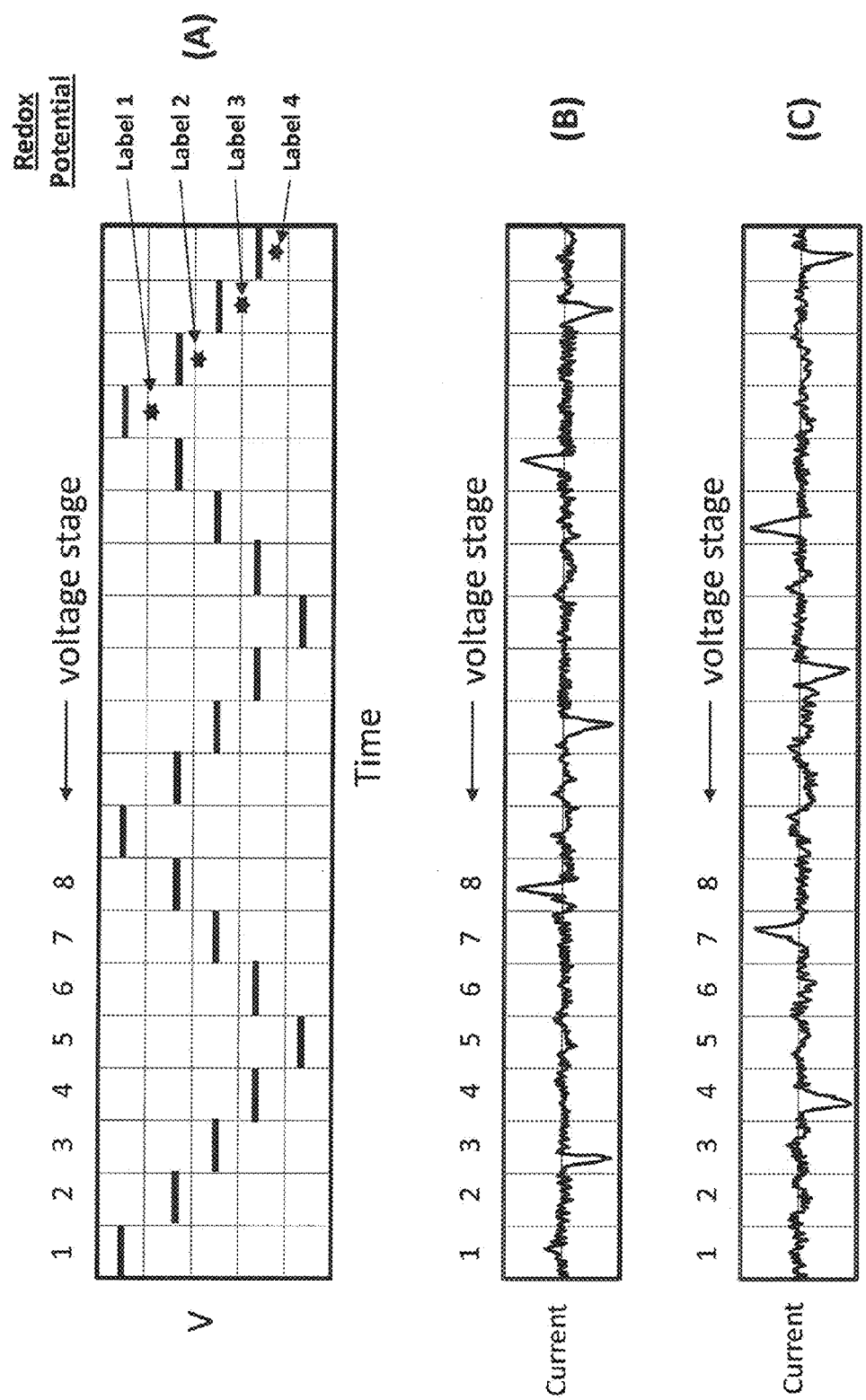
FIG. 9(A) shows exemplary voltages versus time applied to a single electrode configuration redox device.
FIG. 9(B) shows the resulting current signal for a nucleotide having redox label 2.
FIG. 9(C) shows the resulting current signal for a nucleotide having redox label 3

FIG. 9 shows an example of how sequencing can be performed with a one electrode configuration using four nucleotide analogs, each having a different redox label that has a different redox potential. A sequencing system is set up as described herein. FIG. 9(A) shows a plot of the applied voltage over time on the one electrode. The electrode is cycled through 8 voltage stages as shown. There are four nucleotide analogs in the sequencing reaction, each having a different redox label with a different redox potential. The redox potentials of the labels are indicated on the figure with a (*). As the voltage is stepped past the label the label can become oxidized or reduced. FIG. 9(B) illustrates how the current at the electrode is detected for the situation where a nucleotide analog having redox label 2 is in the active site and therefore proximate to the electrode. At voltage stage 1, a label that is present proximate to the electrode is in its reduced form. As the voltage steps from voltage stage 2 to voltage stage 3, this voltage drops below the redox potential of redox label 2. During voltage stage 3, at some point, the label will diffuse close enough to the electrode for electron transfer and oxidation. A negative current peak indicative of oxidation is observed during voltage step 3. The voltage steps continue down through voltage step 5, then up, until, at voltage step 8, the voltage is above the redox potential of label 2, and the oxidized form of label 2 will be reduced, resulting in a positive current peak during voltage stage 8. The appearance of a negative current at voltage step 3 and a positive current at voltage step 8 is thus characteristic of the presence of label 2 in the active site of the enzyme.

FIG. 9(C) shows a similar plot to FIG. 9(B), where the nucleotide in the active site of the enzyme bears redox label 3. Analogous to the situation above, for redox label 3, the characteristic currents are a negative current during voltage step 4 and a positive current during voltage step 7. Thus, using this approach, the presence of each of the four redox labels proximate to the electrode can be detected. As described above for the two electrode system, the time frame for voltage stepping can be varied, and that typically it is desired that the time for cycling through the voltage steps be short as compared to the average (or median) time that a label on an incorporated nucleotide analog spends in the active site of the enzyme. In some cases the time for cycling through the voltage stages is more than 10 times less than the average (or median) time for incorporation. In some cases the time for cycling through the voltage stages is more than 100 times less than the average (or median) time for incorporation. In some cases the time for cycling through the voltage stages is more than 1000 times less than the average (or median) time for incorporation. As described above for the two electrode configuration, current amplitude or current oscillation color or combinations can be incorporated to identify incorporated nucleotide analogs.

As described above, one can increase the amplitude of the current signal by using multiple redox labels on a nucleotide analog. The use of multiple labels on an analog can be particularly useful for carrying out the one electrode method. Having multiple labels increases the current that is measured within a voltage step. For example, with the one electrode method, all of the nucleotides in the sequencing mixture have from 2 to 1,000 redox labels. In some cases, all of the nucleotides in the sequencing mixture have from 4 to 100 redox labels. In some cases, all of the nucleotides in the sequencing mixture have from 5 to 20 redox labels.

Another timescale to consider with respect to carrying out the methods of the invention is the diffusion timescale, and in particular, the mean time between redox events for a tethered redox label. The tethered redox label will diffuse and sample a volume that is bounded by the length of the tether. Within this volume is a region near the electrodes where redox reactions with the electrode will occur. As described herein in reference to current oscillation color, the diffusion profile of the redox probe can be controlled by controlling parameters such as the length of the tether to the surface (including the nucleotide analog to which the redox label is connected, the polymerase enzyme with which the nucleotide analog is associated, and the attachment moiety that attaches the polymerase enzyme to the substrate), the spring constant of the tether including the linker, the proximity of the enzyme to the electrode(s), solution viscosity, and geometry factors including the three dimensional form of the electrode(s). It is typically desired that the time frame of the voltage steps be long with respect to the median diffusion time. For the two electrode system, or for the one electrode systems with solution phase cycling redox agent, where it is desirable to have multiple oxidations and reductions it can be desirable to have the voltage step time be quite long as compared to the median diffusion time. For example, the voltage step time is from 10 times to 100,000 times the voltage step time, or from 100 times to 10,000 times the voltage step time. For the one electrode configuration without redox cycling, the voltage step time can be closer to the median diffusion time. For example, the voltage step time is from 2 times to 100 times the median diffusion time, or from 4 times to 20 times the median diffusion time. Where there are multiple redox labels per nucleotide analog, a longer voltage step time as compared to the median diffusion time may be used to account for the reduction or oxidation of each of the multiple redox labels. While the voltage step time is usually greater than the average diffusion time, in some cases, the voltage step time can be shorter than the average diffusion time.

Calculations indicate that for a 10 nm tether, the median diffusion time is on the order of 20 nanoseconds. Thus, for a 200 microsecond voltage step time, the average number of excursions within the region for a redox reaction is on the order of 10,000. This number of excursions allows for thousands of electrons to be detected. These times can be varied in order to improve desired parameters such as signal to noise, measurement frequency, and signal throughput.

Figure 10:
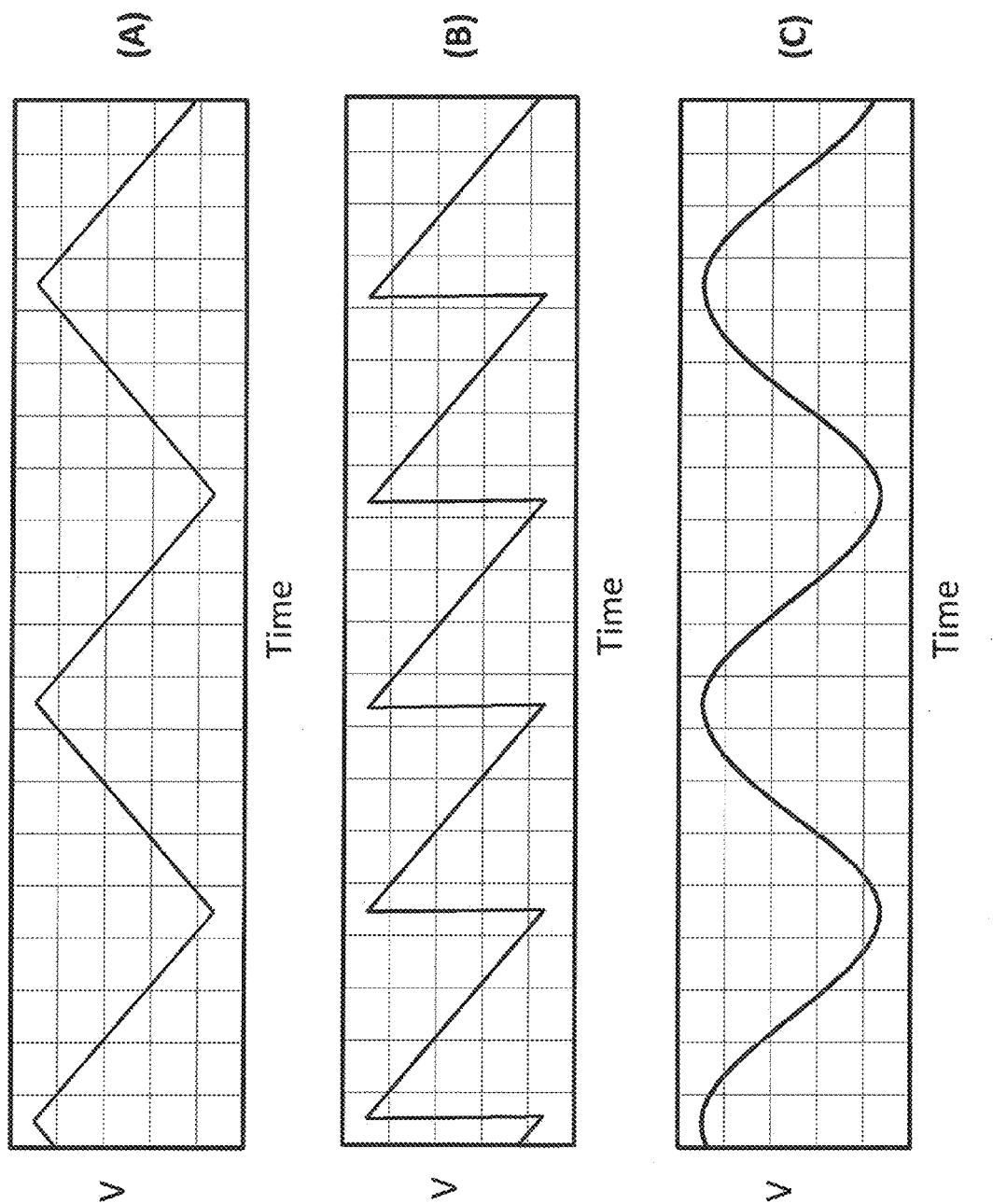
FIG. 10(A) shows an exemplary waveform that can be used for the one or two electrode configurations of redox devices.
FIG. 10(B) shows an alternative exemplary waveform that can be used for the one or two electrode configurations of redox devices.
FIG. 10(C) shows an alternative exemplary waveform that can be used for the one or two electrode configurations of redox devices.

The exemplary methods described above use discrete voltage steps resulting in stair step voltage profiles. Discrete steps are useful for illustrating the methods of the invention, and in some cases discrete steps can be useful for producing a robust detection system. It is to be understood, however, that any suitable waveform of voltage on the one or two electrodes can be used. FIG. 10 illustrates some waveforms that can be applied in the methods of the invention. FIG. 10(A) shows a linear ramp waveform, FIG. 10(B) shows a saw tooth waveform, and FIG. 10(C) shows a sine wave form. These waveforms can be applied for either the one electrode or the two electrode configuration. For the two electrode configuration, typically identical but voltage offset waveforms will be applied to each of the top and bottom electrodes, for example, in phase sine waves on each of the top and bottom electrode offset by a fixed voltage. The fixed voltage can be, for example, from 0.1 V to 1.0 V. It is also appreciated that waveforms of different frequencies, amplitudes, DC offsets and other characteristics can be applied to the different electrodes, resulting in complex patterns of redox cycling and stagnation that will depend on the redox potential of the label relative to the two. Any pattern of applied voltages to the two electrodes that leads to some periods of cycling and other periods of stagnation in a pattern than is different for the different redox labels can be used to detect and differentiate the different labels. The invention encompasses all of these methods. In addition, any suitable approach to determining the presence of a label by redox potential such as cyclic voltammetry, pulse voltammetry, or square wave voltammetry can be used.

The nanoscale electrodes of the invention are typically prepared such that the electrodes have low capacitance in order to allow for rapidly changing the voltage on the electrodes to carry out the sequencing methods described herein. The resistance and capacitance are kept low by the selection of materials and by the geometry of the electrodes and the spacing of the electrodes. One of the considerations is keeping the RC time constant of each redox device low enough to allow for changing the voltage on the electrodes to carry out the methods described herein. In some cases, the RC time constant for the electrode is less than 100 microseconds, less than 10 microseconds, less than 1 microsecond, less than 0.1 microseconds, or less than 0.01 microseconds. In some cases, the RC time constant is between 0.01 microseconds and 100 microseconds. In order to keep the RC time constant low, the electrodes and the interconnects that carry current to and from the electrodes are formed from a material having an electrical conductivity of greater than 106 S/m. Suitable materials include copper, silver, gold, platinum, and aluminum. In order to keep the capacitance low, the dimensions of the electrodes are also generally small—on the nanometer scale. In addition, where there are two electrodes near each other as in the two electrode configuration, while the electrode portions exposed to the surface are close together, the electrodes are configured not to have large portions where the two electrodes are within a few nanometers. For example, for the two electrode configuration illustrated in FIG. 7(F), the electrode structures are close together near the region where they are exposed and where the electrochemistry will occur in order for the tethered label to be able to reach both electrodes, but the electrodes taper away from each other within the structure in order to minimize capacitance. It is also an aspect of the invention to minimize the area of electrodes that is in contact with conductive liquid so as to minimize the capacitance. Similarly it is an aspect of the invention to use insulating layers to increase the distance to ground planes, other electrodes, or any other conductor which could produce stray capacitance.

The ability to electrically address the small redox devices of the instant invention quickly due to the low RC time constant of the structures is useful for carrying out the invention as it allows for sampling multiple redox regions to identify the identity of the different redox components that are present.

The methods described herein provide for identifying the nucleotide analogs that are incorporated in to a growing nucleic acid strand as they are incorporated in the bound polymerase-template complex. The presence and identity of the bases is measured by measuring redox current in electrodes proximate to the bound polymerase-template complex. As described above, the presence of a redox label corresponding to a particular base proximate to a redox electrode for a period of time corresponding to the time for base incorporation indicates that that base has been incorporated. The incorporation of that base into the growing strand indicates the presence of the complementary base in the template strand, providing sequence information about the template. The calling of bases is done using software that takes the current versus time information, and in some cases other information in order to call the base that has been incorporated.

An exemplary process for pulse recognition is as follows. Once the current traces have been generated for a given redox device for a certain time period, the current traces are subjected to a pulse recognition process. In the initial step, a baseline is established for the trace. Typically, the baseline may comprise signal contributions from a number of background sources (depending on the details of the spectral and trace extraction steps). For example, such noise can include, e.g., global background (e.g. large scale spatial cross-talk) and diffusion background. These backgrounds are generally stable on the timescales of pulses, but still may vary slowly over longer timescales. Baseline removal comprises any number of techniques, ranging from, e.g.: a median of the trace, running lowest-percentile with bias correction, polynomial and/or exponential fits, or low-pass filtering with an FFT. Generally these methods will attempt to be robust to the presence of pulses in the trace and may actually be derived at through iterative methods that make multiple passes at identifying pulses and removing them from consideration of baseline estimation. In certain preferred embodiments, a baseline or background model is computed for each trace channel, e.g., to set the scale for threshold-based event detection.

Other baselining functions include correction for drift or decay of overall signal levels. For example, global background decay is sometimes observed. This global background decay is present on portions of the substrate at which there is no enzyme bound proximate to nanoscale electrodes (control electrodes), thus allowing the traces derived from these locations to be used in combination with the two dimensional global background image to estimate the contribution of this signal to every trace/channel across the chip. This component of variability can then be subtracted from each trace and is usually very effective at removing this decay. Typically, this is carried out prior to the baselining processes.

Following establishment of the baseline the traces are subjected to noise suppression filtering to maximize pulse detection. In particularly preferred aspects, the noise filter is a 'matched filter' that has the width and shape of the pulse of interest. While current pulse timescales (and thus, pulse widths) are expected to vary among different redox labeled nucleotides, the preferred filters will typically look for pulses that have a characteristic shape with varying overall duration. For example, a boxcar filter that looks for a current pulse of prolonged duration, e.g., from about 10 ms to 100 or more ms, provides a suitable filter. This filtering is generally performed in the time-domain through convolution or low-pass frequency domain filtering. Other filtering techniques include: median filtering (which has the additional effect of removing short timescale pulses completely from the trace depending on the timescale used), and Savitsky-Golay filtering which tends to preserve the shape of the pulse—again depending on the parameters used in the filter).

Although described in terms of a generic filtering process across the various traces, it will be appreciated that different pulses may have different characteristics, and thus may be subjected to trace specific filtering protocols. For example, in some cases, a given redox labeled analog (e.g., A) may have a different pulse duration for an incorporation event than another different redox labeled analog (e.g., T). As such, the filtering process for the spectral trace corresponding to the A analog will have different filtering metrics on the longer duration pulses, than for the trace corresponding to the T analog incorporation. In general, such filters (e.g., multi-scale filters) enhance the signal-to-noise ratio for enhanced detection sensitivity. Even within the same channel there may be a range of pulse widths. Therefore typically a bank of these filters is used in order to maximize sensitivity to pulses at a range of timescales within the same channel.

In identifying pulses on a filtered trace, a number of different criteria can be used. For example, one can use absolute current amplitude, either with or without normalization. Alternatively, one can identify pulses from the pulse to diffusion background ratio as a metric for identifying the pulse. In still other methods, one may use statistical significance tests to identify likely pulses over the background noise levels that exist in a given analysis. The latter method is particularly preferred as it allows for variation in potential pulse intensities, and reduces the level of false positives called from noise in the baseline.

As noted previously, a number of signal parameters including current amplitude, redox potential, residence time, and current oscillation color may be and generally are used in pulse identification (as well as in pulse classification). For purposes of illustration, the discussion below primarily on the use of two pulse metrics, namely pulse intensity and pulse width. As will be appreciated, the process may generally include any one or more of the various pulse metric comparisons set forth elsewhere herein.

As such, following filtering, standard deviation of the baselines (noise and current pulses) and determination of pulse detection thresholds are carried out. Preferred methods for determining the standard deviation of a trace include robust standard deviation determinations including, e.g., being based upon the median absolute difference about the baseline, a Gaussian or Poisson fit to the histogram of baselined intensities, or an iterative sigma-clip estimate in which extreme outliers are excluded. Once determined for each trace, a pulse is identified if it exceeds some preset number of standard deviations from the baseline. The number of standard deviations that constitute a significant pulse can vary depending upon a number of factors, including, for example, the desired degree of confidence in identification or classification of significant pulses, the signal to noise ratio for the system, the amount of other noise contributions to the system, and the like. In a preferred aspect, the up-threshold for an incorporation event, e.g., at the initiation of a pulse in the trace, is set at about 5 standard deviations or greater, while the down-threshold (the point at which the pulse is determined to have ended) is set at 1.25 standard deviations. Up thresholds can be used as low as 3.75 standard deviations and as high as the signal-to-noise ratio will allow—up to 7, 10, 20 or 50 standard deviations. The down threshold can be set anywhere from minus 1 standard deviation up to the up threshold. Alternatively, the down threshold can be computed from the mean and standard deviation of the up signal, in which case it could be set between minus 3 standard deviations to minus 6 standard deviations. If the signal-to-noise ratio is sufficiently high it could be set to minus 7, 10, 20 or 50 standard deviations. The pulse width is then determined from the time between the triggering of the up and down thresholds. Once significant pulses are initially identified, they are subjected to further processing to determine whether the pulse can be called as a particular base incorporation. Alternatively the signals can be filtered ahead of time to eliminate frequency components that correspond to timescales not likely to correspond to true incorporation events, in which case the further processing steps are optional.

In some cases, multiple passes are made through traces examining pulses at different timescales, from which a list of non-redundant pulses detected at such different time thresholds may be created. This typically includes analysis of unfiltered traces in order to minimize potential pulse overlap in time, thereby maximizing sensitivity to pulses with width at or near the highest frame rate of the camera. This allows the application of current oscillation color or other metrics to current pulses that inherently operate on different timescale. In particular, an analysis at longer timescales may establish trends not identifiable at shorter timescales, for example, identifying multiple short timescale pulses actually correspond to a single longer, discrete pulse.

In addition, some pulses may be removed from consideration/evaluation, where they may have been identified as the result of systematic errors, such as through spatial cross-talk of adjacent redox devices, or cross-talk between detection channels (to the extent such issues have not been resolved in a calibration processes). Typically, the calibration process will identify cross-talk coefficients for each redox device, and thus allow such components to be corrected.

In certain embodiments, a trace-file comprises L-weighted-sum (LWS) traces, where trace is optimized to have maximum pulse detection sensitivity to an individual redox label in the reaction mixture. This is not a deconvolved or multicomponent trace representation, and suffers from spectral cross-talk.

Classification of an extracted pulse into one of the 4(or N) redox labels is then carried out by comparing the extracted spectrum to the spectra of the redox labels sets established in a calibration process. A number of comparative methods may be used to generate a comparative metric for this process. For example, in some aspects, a $\chi^2$ test is used to establish the goodness of fit of the comparison. A suitable $\chi^2$ test is described, for example, in U.S. Patent Application 20120015825, incorporated herein by reference for all purposes.

Once the pulse spectrum is classified as corresponding to a particular label spectrum, that correlation is then used to assign a base classification to the pulse. As noted above, the base classification or "calling" may be configured to identify directly the redox-tag labeled base added to the extended primer sequence in the reaction, or it may be set to call the complementary base to that added (and for which the pulse spectrum best matches the label spectrum). In either case, the output will be the assignment of a base classification to each recognized and classified pulse. For example, a base classification may be assignment of a particular base to the pulse, or identification of the pulse as an insertion or deletion event.

In an ideal situation, once a pulse is identified as significant and its spectrum is definitively identified, a base is simply called on the basis of that information. However, as noted above, in typical sequencing runs, signal traces can include signal noise, such as missing pulses (e.g., points at which no pulse was found to be significant, but that correspond to an incorporation event) false positive pulses, e.g., resulting from nonspecifically adsorbed analogs or labels, or the like. Accordingly, pulse classification (also termed base classification) can in many cases involve a more complex analysis. As with pulse identification, above, base classification typically relies upon a plurality of different signal characteristics in assigning a base to a particular identified significant pulse. In many cases, two, three, five, ten or more different signal characteristics may be compared in order to call a base from a given significant pulse. Such characteristics include those used in identifying significant pulses as described above, such as pulse width or derivative thereof (e.g., smooth pulse width estimate, cognate residence time, or non-cognate residence time), pulse intensity, pulse channel, estimated average current amplitude of pulse, median current amplitude of all pulses in the trace corresponding to the same channel, background and/or baseline level of channel matching pulse identity, signal to noise ratio (e.g., signal to noise ratio of pulses in matching channel, and/or signal to noise ratio of each different channel), power to noise ratio, integrated counts in pulse peak, maximum signal value across pulse, pulse density over time (e.g., over at least about 1, 2, 5, 10, 15, 20, or 30 second window), shape of and distance/time to neighboring pulses (e.g., interpulse distance), channel of neighboring pulses (e.g., channel of previous 1, 2, 3, or 4 pulses and/or channel of following 1, 2, 3, or 4 pulses), similarity of pulse channel to the channel of one or more neighboring pulses, signal to noise ratio for neighboring pulses; spectral signature of the pulse, pulse centroid location, and the like, and combinations thereof. Typically, such comparison will be based upon standard pattern recognition of the metrics used as compared to patterns of known base classifications, yielding base calls for the closest pattern fit between the significant pulse and the pattern of the standard base profile.

Comparison of pulse metrics against representative metrics from pulses associated with a known base identity will typically employ predictive or machine learning processes. In particular, a "training" database of "N previously solved cases" is created that includes the various metrics set forth above. For example, a vector of features is analyzed for each pulse, and values for those features are measured and used to determine the classification for the pulse, e.g., an event corresponding to the pulse, e.g., an incorporation, deletion, or insertion event. As used herein, an incorporation event refers to an incorporation of a nucleotide complementary to a template strand, a deletion event corresponds to a missing pulse resulting in a one position gap in the observed sequence read, and an insertion event corresponds to an extra pulse resulting in detection of a base in the absence of incorporation. For example, an extra pulse can be detected when a polymerase binds a cognate or noncognate nucleotide but the nucleotide is released without incorporation into a growing polynucleotide strand. From that database, a learning procedure is applied to the data in order to extract a predicting function from the data. A wide variety of learning procedures are known in the art and are readily applicable to the database of pulse metrics. These include, for example, linear/logistic regression algorithms, neural networks, kernel methods, decision trees, multivariate splines (MARS), multiple additive regression trees (MART™), support vector machines.

In addition to calling bases at pulses identified as significant, the present methods also allow for modeling missing pulses. For example, conditional random fields (CRF) are probabilistic models that can be used to in pulse classification (see, e.g., Lafferty, et al. (2001) Proc. Intl. Conf. on Machine Learning 01, pgs 282-289, incorporated herein by reference in its entirety for all purposes). A CRF can also be conceptualized as a generalized Hidden Markov Model (HMM), some examples of which are described elsewhere herein and are well known in the art. The present invention includes the use of CRFs to model missing bases in an observed pulse trace. In addition to base calling, algorithms for consensus generation and sequence alignment can be used to obtain further information from the sequencing methods described herein.

Methods for calling bases, consensus generation, and sequence alignment are described, for example, in the following patents and applications, which are incorporated herein for all purposes: U.S. Pat. No. 7,995,202 Methods and Systems for Simultaneous real-time monitoring of optical signals from multiple sources; U.S. Pat. No. 7,626,704 Methods and systems for simultaneous real-time monitoring of optical signals from multiple sources; U.S. Pat. No. 8,182,993 Methods and Processes for Calling Bases in Sequence by Incorporation Methods; U.S. Ser. No. 13/468,347 filed May 10, 2012, Algorithms for Sequence Determination; US 20120015825 Analytical Systems and Methods with Software Mask; US 20110257889 Sequence Assembly and Consensus Sequence Determination; US 20120052490 Methods and Systems for Monitoring Reactions; US 20100169026 Algorithms for Sequence Determination Processing the data. While the base identification and base calling algorithms in the above documents are typically described referring to optical systems, in light of the current specification, one of ordinary skill in the art would understand how to bring such methods to bear in the redox sequencing systems and methods of the present invention.

Polymerase-Nucleic Acid Complex

The polymerase-enzyme complex of the invention comprises a nucleic acid polymerase enzyme associated with a template molecule. The template also typically has a primer hybridized to it, while some polymerase enzymes can initiate nucleic acid synthesis without the addition of an external primer. While many enzyme-substrate interactions are transient, some polymerase enzymes can form relatively stable complexes with nucleic acids that can be manipulated, purified, and then subsequently used to carry out nucleic acid synthesis. For example, DNA polymerases having relatively high processivity can have strong associations with template nucleic acid molecules. An exemplary DNA Polymerase is phi-29 DNA polymerase. Methods for forming and manipulating polymerase-nucleic acid complexes are described, for example in copending U.S. patent application entitled Purified Extended Polymerase/Template Complex for Sequencing" 61/385,376, filed Sep. 22, 2010 and U.S. patent application Ser. No. 13/427,725 filed Mar. 22, 2012 entitled "Isolation of Polymerase-Nucleic Acid Complexes" which is incorporated by reference herein in its entirety for all purposes.

The polymerase-nucleic acid complex will typically comprise a polymerase and a nucleic acid having a double stranded region. The polymerase-nucleic acid complex will generally have a primer from which a nascent nucleic acid strand will be produced complementary to a template strand of the nucleic acid. The primer is usually a short oligonucleotide that is complementary to a portion of the template nucleic acid. The primers of the invention can comprise naturally occurring RNA or DNA oligonucleotides. The primers of the invention may also be synthetic analogs. The primers may have alternative backbones as described above for the nucleic acids of the invention. The primer may also have other modifications, such as the inclusion of heteroatoms, the attachment of redox labels, or substitution with functional groups which will still allow for base pairing and for recognition by the enzyme. Primers can select tighter binding primer sequences, e.g., GC-rich sequences, as well as employ primers that include within their structure non-natural nucleotides or nucleotide analogs, e.g., peptide nucleic acids (PNAs) or locked nucleic acids (LNAs), that can demonstrate higher affinity pairing with the template. In some cases, the primer is added as a separate component to form the complex; in other cases, the primer can be part of the nucleic acid that used. For example, in some cases priming can begin at a nick or a gap in one strand of a double-stranded nucleic acid.

The template nucleic acid can be derived from any suitable natural or synthetic source. In preferred embodiments, the template comprises double stranded DNA, but in some circumstances double-stranded RNA or RNA-DNA heteroduplexes can be used. The template nucleic acid can be genomic DNA from eukaryotes, bacteria, or archaea. The template nucleic acid can be cDNA derived from any suitable source including messenger RNA. The template nucleic acid can comprise a library of double stranded segments of DNA. The template nucleic acid can be linear or circular. For example, the nucleic acid can be topologically circular and have a linear double stranded region. A circular nucleic acid can be, for example, a gapped plasmid. In some embodiments the nucleic acid is a double stranded linear DNA having a gap in one of the strands. The gap provides a site for attachment of the polymerase enzyme for nucleic acid synthesis. The linear double stranded DNA having a double-stranded DNA adaptor can be made by ligation of DNA fragment to an adaptor through blunt end—ligation or sticky end ligation. The ligation produces a linear DNA having a gap close to the 5' end of one or both of the strands. The gap can be any suitable width. For example, the gap can be from 1 to 50 bases, from 2 to 30 bases, or from 3 to 12 bases.

The terms "nucleic acid" or "oligonucleotide" or grammatical equivalents herein mean at least two nucleotides covalently linked together. A nucleic acid of the present invention will generally contain phosphodiester bonds, although in some cases, nucleic acid analogs are included that may have alternate backbones, comprising, for example, phosphoramide, phosphorothioate, phosphorodithioate, and peptide nucleic acid backbones and linkages. Other analog nucleic acids include those with positive backbones, non-ionic backbones, and non-ribose backbones, including those described in U.S. Pat. Nos. 5,235,033 and 5,034,506. The template nucleic acid may also have other modifications, such as the inclusion of heteroatoms, the attachment of redox labels, or substitution with functional groups which will still allow for base pairing and for recognition by the enzyme.

The template sequence may be provided in any of a number of different format types depending upon the desired application. The template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220,674, filed Jul. 25, 2008. Alternate functional circular constructs are also described in U.S. patent application Ser. No. 12/383,855, filed Mar. 27, 2009, and U.S. Pat. No. 8,153,375 Compositions and Methods for Nucleic Acid Sequencing; U.S. Pat. No. 8,003,330 Error-Free Amplification of DNA for Clonal Sequencing; and Ser. No. 13/363,066 filed Jan. 31, 2012 Methods and Compositions for Nucleic Acid Sample Preparation, the full disclosures of each of which are incorporated herein by reference in their entirety for all purposes.

Briefly, such alternate constructs include template sequences that possess a central double stranded portion that is linked at each end by an appropriate linking oligonucleotide, such as a hairpin loop segment. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

The nucleic acids can comprise a population of nucleic acids having universal sequence regions that are common to all of the nucleic acids in the population and also have specific regions that are different in the different members of the population. The current invention allows for capturing and isolating polymerase-nucleic acid complexes using either the universal or the specific regions.

While in many cases nucleic acid synthesis is describe herein as extending from a primer, it is to be understood that some polymerases do not require an added external primer, and can be initiated using terminal protein. Polymerases that can be initiated using terminal protein include phi-29 polymerase.

Polymerase Enzymes

Polymerase enzymes useful in the invention include polymerases mutated to have desirable properties for sequencing.

For example, suitable enzymes include those taught in, e.g., 61/593,569 filed Feb. 1, 2012 Recombinant Polymerases with Increased Phototolerance; US 20120034602 Recombinant Polymerases for Improved Single Molecule Sequencing; US 20100093555 Enzymes Resistant to Photodamage; US 20110189659 Generation of Modified Polymerases for Improved Accuracy in Single Molecule Sequencing; US 20100112645 Generation of Modified Polymerases for Improved Accuracy in Single Molecule Sequencing; US 2008/0108082 Polymerase enzymes and reagents for enhanced nucleic acid sequencing; US 20110059505 Polymerases for Nucleotide Analogue Incorporation; and U.S. Provisional Patent No. 61/708,469 filed Oct. 1, 2012, all of which are incorporated by reference herein for all purposes. The modified polymerases can have modified properties such as e.g., decreased branch fraction formation, improved specificity, improved processivity, altered rates, improved retention time, improved stability of the closed complex, etc.

In addition, the polymerases can be further modified for application-specific reasons, such as to increase photostability, e.g., as taught in U.S. patent application Ser. No. 12/384,110 filed Mar. 30, 2009, by Keith Bjornson et al. entitled "Enzymes Resistant to Photodamage," to improve activity of the enzyme when bound to a surface, as taught, e.g., in WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al., or to include purification or handling tags as is taught in the cited references and as is common in the art. While the current method does not typically include light illumination, there is generally no issue with photostability. However, it will be understood that the electron transfer processes of electrochemistry can create reactive species analogous to reactive species formed during photonic excitation. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

The polymerase enzymes used in the invention will generally have strand-displacement activity. Many polymerases have this capability, and it is useful in the context of the current invention for opening up and exposing the regions of a nucleic acid sample for capture by a hook molecule. In some cases, strand displacement is part of the polymerase enzyme itself. In other cases, other cofactors or co-enzymes can be added to provide the strand displacement capability.

DNA Polymerases

DNA polymerases are sometimes classified into six main groups based upon various phylogenetic relationships, e.g., with E. coli Pol I (class A), E. coli Pol II (class B), E. coli Pol III (class C), Euryarchaeotic Pol II (class D), human Pol beta (class X), and E. coli UmuC/DinB and eukaryotic RAD30/xeroderma pigmentosum variant (class Y) which are incorporated by reference herein for all purposes. For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1):reviews 3002.1-3002.4; and Steitz (1999) "DNA polymerases: structural diversity and common mechanisms" J Biol Chem 274:17395-17398, which are incorporated by reference herein for all purposes. The basic mechanisms of action for many polymerases have been determined. The sequences of literally hundreds of polymerases are publicly available, and the crystal structures for many of these have been determined, or can be inferred based upon similarity to solved crystal structures of homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296) which are incorporated by reference herein for all purposes. In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.) which are incorporated by reference herein for all purposes. Any of these available polymerases can be modified in accordance with the invention to decrease branching fraction formation, improve stability of the closed polymerase-DNA complex, and/or alter reaction rate constants.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHI™ Φ29 DNA Polymerase, available from Epicentre Biotechnologies; PfuUltra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, E. coli DNA Polymerase 1, Klenow fragment, reverse transcriptases, Φ29-related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204 which are incorporated by reference herein for all purposes. Alternately, the modified recombinant DNA polymerase can be homologous to other Φ29-type DNA polymerases, such as B103, GA-1, PZA, Φ15, BS32, M2Y, Nf, Gl, Cp-1, PRD1, PZE, SFS, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases are described, for example, in U.S. patent application Ser. No. 12/924,701, filed Sep. 30, 2010; and Ser. No. 12/384,112, filed Mar. 30, 2009 which is incorporated by reference herein for all purposes.

RNA Dependent RNA Polymerases

In some embodiments, the polymerase enzyme that is used for sequencing is an RNA polymerase. Any suitable RNA polymerase (RNAP) can be used including RNA polymerases from bacteria, eukaryotes, viruses, or archea. Suitable RNA polymerases include RNA Pol I, RNA Pol II, RNA Pol III, RNA Pol IV, RNA Pol V, T7 RNA polymerase, T3 RNA polymerase or SP6 RNA polymerase. The use of RNA polymerases allows for the direct sequencing of messenger RNA, transfer RNA, non-coding RNA, ribosomal RNA, micro RNA or catalytic RNA. Where RNA polymerases are used, the polymerizing reagents will generally include NTPs or their analogs rather than the dNTPs used for DNA synthesis. In addition, RNA polymerases can be used with specific cofactors. There are many proteins that can bind to RNAP and modify its behavior. For instance, GreA and GreB from E. coli and in most other prokaryotes can enhance the ability of RNAP to cleave the RNA template near the growing end of the chain. This cleavage can rescue a stalled polymerase molecule, and is likely involved in proofreading the occasional mistakes made by RNAP. A separate cofactor, Mfd, is involved in transcription-coupled repair, the process in which RNAP recognizes damaged bases in the DNA template and recruits enzymes to restore the DNA. Other cofactors are known to play regulatory roles; i.e., they help RNAP choose whether or not to express certain genes. RNA dependent RNA polymerases (RNA replicases) may also be used including viral RNA polymerases: e.g. poliovirul 3Dpol, vesicular stomatitis virus L, and hepatitis C virus NS5b protein; and eukaryotic RNA replicases which are known to amplify microRNAs and small temporal RNAs and produce double-stranded RNA using small interfering RNAs as primers.

Reverse Transcriptases

The polymerase enzyme used in the methods or compositions of the invention includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal RNA, micro RNA or catalytic RNA.

Thus, any suitable polymerase enzyme can be used in the systems and methods of the invention. Suitable polymerases include DNA dependent DNA polymerases, DNA dependent RNA polymerases, RNA dependent DNA polymerases (reverse transcriptases), and RNA dependent RNA polymerases.

Immobilization of the Polymerase-Template Complex

The polymerase-template complex can be attached to the surface by binding the polymerase, the template nucleic acid, or a primer. The binding can be either covalent or non-covalent. In some cases, an $SiO_2$ region of the surface can be selectively functionalized to bind the polymerase complex. The selective functionalization of $SiO_2$ can be done, for example, using silane chemistry. For example, the $SiO_2$ portion of the surface can be selectively treated with a biotin functionalized silane, and the surface can be treated with an enzyme complex attached to streptavidin. The streptavidin-polymerase-template complex will bind specifically to the biotin on the $SiO_2$ portions of the surface providing selective binding. See e.g. U.S. Pat. No. 8,193,123 which is incorporated herein by reference for all purposes. In some cases, small regions, e.g. balls, islands, or pits can be made on the surface that allow only a small number, and in some cases allow only a single polymerase enzyme to bind. The creation of regions to bind a single polymerase enzyme complex are described, for example in U.S. Patent Application 20100009872 Single Molecule Loading Methods and Compositions; and U.S. Patent Application 20110257040 Nanoscale Apertures Having Islands of Functionality which are incorporated herein by reference for all purposes. DNA molecules typically possess a strong negative charge and can thus be directed using electric fields in aqueous solution. Because the devices of the instant invention contemplate arrays of electrodes with means of applying electric potentials and simultaneously measuring currents from proximate labels, the capability exists to use the potential-setting capacity to attract polymerases bound to DNA molecules to the electrode region and then either simultaneously or in alternating periods check to see if a polymerase has bound the system. In this way each active device can be loaded with a single polymerase by ceasing the attractive potential when the binding of a DNA-Polymerase complex is detected.

The immobilization of a component of an analytical reaction can be engineered in various ways. For example, an enzyme (e.g., polymerase, reverse transcriptase, kinase, etc.) may be attached to the substrate at a reaction site, e.g., proximate to a nanoscale electrode. In other embodiments, a substrate in an analytical reaction (for example, a nucleic acid template, e.g., DNA, RNA, or hybrids, analogs, and mimetics thereof, or a target molecule for a kinase) may be attached to the substrate at a reaction site. Certain embodiments of template immobilization are provided, e.g., in U.S. patent application Ser. No. 12/562,690, filed Sep. 18, 2009 and incorporated herein by reference in its entirety for all purposes. One skilled in the art will appreciate that there are many ways of immobilizing nucleic acids and proteins, whether covalently or non-covalently, via a linker moiety, or tethering them to an immobilized moiety. These methods are well known in the field of solid phase synthesis and micro-arrays (Beier et al., Nucleic Acids Res. 27:1970-1-977 (1999)). Non-limiting exemplary binding moieties for attaching either nucleic acids or polymerases to a solid support include streptavidin or avidin/biotin linkages, carbamate linkages, ester linkages, amide, thiolester, (N)-functionalized thiourea, functionalized maleimide, amino, disulfide, amide, hydrazone linkages, among others. Antibodies that specifically bind to one or more reaction components can also be employed as the binding moieties. In addition, a silyl moiety can be attached to a nucleic acid directly to a substrate such as glass using methods known in the art.

In some embodiments, a nucleic acid template is immobilized onto a reaction site (e.g., proximate to a redox electrode) by attaching a primer comprising a complementary region at the reaction site that is capable of hybridizing with the template, thereby immobilizing it in a position suitable for monitoring. In certain embodiments, an enzyme complex is assembled, e.g., by first immobilizing an enzyme component. In other embodiments, an enzyme complex is assembled in solution prior to immobilization. Where desired, an enzyme or other protein reaction component to be immobilized may be modified to contain one or more epitopes for which specific antibodies are commercially available. In addition, proteins can be modified to contain heterologous domains such as glutathione S-transferase (GST), maltose-binding protein (MBP), specific binding peptide regions (see e.g., U.S. Pat. Nos. 5,723,584, 5,874,239 and 5,932,433), or the Fc portion of an immunoglobulin. The respective binding agents for these domains, namely glutathione, maltose, and antibodies directed to the Fc portion of an immunoglobulin, are available and can be used to coat the surface of a redox device of the present invention. The binding moieties or agents of the reaction components they immobilize can be applied to a support by conventional chemical techniques which are well known in the art. In general, these procedures can involve standard chemical surface modifications of a support, incubation of the support at different temperature levels in different media comprising the binding moieties or agents, and possible subsequent steps of washing and cleaning.

The various components of the surface of the redox devices can be selectively treated in order to bind the polymerase-template complex to a specific portion of the substrate. Selective treatment and immobilization is described, for example, in U.S. Pat. No. 5,624,711; U.S. Pat. No. 5,919,523; Hong et al., (2003) Langmuir 2357-2365; U.S. Pat. No. 5,143,854; U.S. Pat. No. 5,424,186; U.S. Pat. No. 8,137,942; U.S. Pat. No. 7,993,891 Reactive surfaces, substrates and methods of producing and using same; U.S. Pat. No. 7,935,310; U.S. Pat. No. 7,932,035 U.S. Pat. No. 7,931,867 Uniform surfaces for hybrid material substrates and methods of making and using same; and U.S. Pat. No. 8,193,123 Articles having localized molecules disposed thereon and methods of producing same, all of which are incorporated herein by reference for all purposes.

The polymerase complex is attached proximate to the electrode or electrodes of the redox device. The attachment is made close enough to the electrode(s) that the redox label on a nucleotide analog held in the active site of the enzyme can extend close enough to the electrode to allow for repeated reduction and oxidation. The polymerase complex can be attached for example from about 1 nm to about 100 nm from a redox electrode, from about 2 nm to about 50 nm from a redox electrode, or from about 4 nm to about 20 nm from a redox electrode. For the two electrode redox device, the polymerase template complex is typically bound to the insulating region between the two electrodes. For the single electrode configuration, the polymerase template complex can be bound, for example, to a region near the electrode, to the electrode, or to an insulating region within or on top of the electrode.

Conditions for Nucleic Acid Synthesis

The conditions required for nucleic acid synthesis are well known in the art. The polymerase reaction conditions include the type and concentration of buffer, the pH of the reaction, the temperature, the type and concentration of salts, the presence of particular additives that influence the kinetics of the enzyme, and the type, concentration, and relative amounts of various cofactors, including metal cofactors. For carrying out the methods of the instant invention, the conditions for polymerase mediated nucleic acid synthesis must also be compatible with conditions for carrying out electrochemistry to detect redox labels. One aspect of carrying out redox chemistry is controlling the ionic strength of the medium. It is know that polymerase enzymes can effectively operate over a range of ionic strengths, and that the ionic strength can be varied by changing the levels of monovalent ions such as Li+, Na+, K+, Rb+, or Cs+. As has been shown the amount of one or more of these cations can have an effect on the kinetics of the polymerase, and that the kinetic behavior can be tuned by varying the relative amounts of these ions. Using combinations of these ions, conditions can be chosen where both the kinetic parameters of the enzyme, and the ionic strength for redox detection can be useful for the instant methods. See, e.g. U.S. Patent Application 20120009567 which is incorporated herein by reference for all purposes. Another consideration for redox detection is that the components of the sequencing reaction mixture should not interfere with the electrochemical detection of the redox labels. For example, the components of the sequencing reaction mixture are generally selected such that they do not have a redox potential in a range whereby they would be oxidized or reduced during the sequencing reaction. Such reagents can be selected by a knowledge of the relevant reduction or oxidation potentials of the component. Tests can readily be performed to confirm that the various components will not interfere with redox detection. Where a desirable component of the reaction mixture may be oxidized or reduced, in some cases, the groups on that component can be modified to reduce or eliminate interference. For example, in some cases a thiol or disulfide portion of a molecule in the reaction mixture may undergo a redox reaction under the conditions of sequencing. In such a case, these groups can be chemically modified in order to reduce or eliminate interference with the redox label electrochemistry.

Enzymatic reactions are often run in the presence of a buffer, which is used, in part, to control the pH of the reaction mixture. Buffers suitable for the invention include, for example, TAPS (3-{[tris(hydroxymethyl)methyl]amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the rate of the polymerase reaction. The temperature of the reaction can be adjusted to enhance the performance of the system. The reaction temperature may depend upon the type of polymerase which is employed.

Nucleotide Analogs

Components of the sequencing reaction mixture include nucleotides or nucleotide analogs. For the methods of the instant invention, at least some of the nucleotide analogs have redox labels attached to them. The nucleotide analogs comprising redox active labels are generally constructed in order to enhance the redox signal when the label is in the enzyme active site. For example, in some cases a linker is used which provides access of the redox label to the electrode when the analog is in the active site. In some cases the redox label is provided with contact to the working electrode while the nucleotide analog is in the active site. In some cases the DNA is tethered and the entire complex diffuses around in reach of physical contact with the electrode to cause a redox cycling signal. In some cases, a long linker on the polymerase is provided such that the polymerase can reach, or be proximate to, two electrodes.

Typically the nucleotide analogs of the invention have the following structure:

Base-Sugar-PP-Linker-Redox Label wherein Base is a nucleobase, Sugar is a sugar such as ribose or deoxyribose, PP is a polyphosphate moiety, Linker is a linking group that extends the length of the nucleotide analog to allow for the redox label do diffuse to the redox electrode to undergo electrochemistry, and the Redox Label is a group that is detectable by electrochemistry at the redox electrode.

Typically there are four nucleotides in the sequencing reaction mixture corresponding to A, G, T, and C for DNA and A, G, C, U for RNA. In some cases, a $5^{th}$, $6^{th}$, or more base is added. In some cases all of the nucleotide analogs have a redox label, in other cases, fewer than all of the nucleotides will have a redox label. In still other cases all of the different nucleotide analog types will carry a redox label, but a particular redox label will be assigned to more than one base type. Typically each of the types of nucleotide will have a nucleotide that is different and can be distinguished from the other nucleotides, for example the other three nucleotides. As described herein, the different nucleotides can have different redox potentials, different current intensities, different current versus time characteristics (current oscillation color), or different combinations of two or more of the above.

The Base is a nucleobase which can be one of the natural bases, a modified natural base or a synthetic base. The Base will selectively associate with its complementary base on the template nucleic acid such that it will be inserted across from its complementary base. The sugar is a group that connects the base to the polyphosphate group. It is typically either ribose or deoxyribose, but can be any sugar or other group that, allows for the complexation and incorporation of the nucleotide analog into the growing strand. PP is a polyphosphate group generally from 2 to 20 phosphates in length, typically from 3 to 12 phosphates in length, and in some preferred embodiments from 4 to 10 phosphates in length. The nucleotide analog can have for example 4, 5, 6, 7 or more phosphate groups. Such nucleotides have been described, for example, in U.S. Pat. Nos. 6,936,702 and 7,041,812, which are incorporated herein by reference for all purposes. Together, the Base, Sugar and PP portion of the nucleotide analog is sometimes referred to as the nucleotide portion or nucleoside phosphate portion.

As used in the art, the term nucleotide refers both to the nucleoside triphosphates that are added to a growing nucleic acid chain in the polymerase reaction, or can refer to the individual units of a nucleic acid molecule, for example the units of DNA and RNA. Herein, the term nucleotide is used consistently with its use in the art. Whether the term nucleotide refers to the substrate molecule to be added to the growing nucleic acid or to the units in the nucleic acid chain can be derived from the context in which the term is used.

The Linker is a linking group that connects the redox label to the nucleotide portion of the nucleotide analog. The linker is typically a long linear or branched moiety whose length and flexibility is used to control the diffusion of the nucleotide analog that is held within the polymerase enzyme while it is being incorporated. The length of the linker is, for example, from between 2 nm and 200 nm when fully extended. It is understood that a long molecule such as a polymer will not spend much time, if any, in its fully extended configuration. The linker can be made up of groups including alkanes, ethers, alcohols, amines, acids, sulfates, sulfonates, phosphates, phosphonates, amides, esters, peptides, and sugars. The groups on the linker can be neutral, positively charged, or negatively charged. In some cases, the linker comprises polyethylene glycol (PEG). It is desirable that the linker have a fixed length (i.e. not be polydisperse) such that the size of any analog molecule in the population will be the same. It is generally desirable that the linker be water compatible in order to encourage the extension of the redox label attached to the linker into a desired diffusion volume such that the redox label samples the region near the electrode in which electrochemistry will occur.

The length of the linker can be chosen for performance with the particular geometry of the redox device that is used. The redox label is tethered to the substrate through the nucleotide analog (comprising the linker), the enzyme and the attachment moiety. The length of this complete tether and the distance of the polymerase complex from the redox electrodes is used in order to select the appropriate linker.

The Redox Label is attached to the nucleotide portion of the nucleotide analog through the linker and phosphate. The linker is typically attached to the terminal phosphate in the polyphosphate moiety, but in some cases can be connected to a phosphate in the polyphosphate chain that is not the terminal phosphate. The linker should be attached to a phosphate that is cleaved on the act of the polymerase enzyme of nucleotide incorporation. The polymerase enzyme cleaves the polyphosphate between the alpha and beta phosphates, thus, the linker should be connected to the beta (second) phosphate or greater.

The redox label may be made up of one or more redox moieties. Acceptable redox labels or moieties can comprise organic compounds, organometallic compounds, nanoparticles, metals, or other suitable substituent. In some cases nanoparticles, each having plurality of redox active molecules is used as a redox label. The redox label should be readily oxidized and reduced repeatedly without significant degradation. The nucleic acid polymerization reaction is typically carried out in an aqueous environment, so the nucleotide analog comprising the redox label should generally be soluble in water. In some cases, charged and polar substituents are present on the redox label to enhance water solubility. Such substituents include carboxylate, sulfate, sulfonate, phosphate, phosphonate, ether, and ester substituents. Where suitable labels are described it is understood that such labels could also include solubilizing substituents. Suitable labels include 1,4-dihydroquinone, 1,4-dihydroxy-2-naphthoic acid, ferrocene, 2,5-dichloro-1,4-benzoquinone, Methylene Blue, Methyl-1,4-benzoquinone, anthraquinone, and nanoparticles such as CdS and ZnS nanoparticles. Suitable labels are described, for example in Levine et al., Biosensors and Bioelectronics, 24, 1995, 2000; Wang et al. J. Am. Chem. Soc. 125, 3214, 2003; Ji et al, J Phys. Chem. C, 1496, 111, 2007; and Kang et al. NPG Asia Materials, doi:10.1038/am2012.1, which are incorporated herein by reference for all purposes.

Redox labels or moities include, for example, ferrocene derivatives such as alkyl ferrocene, ferrocene acetate, alkyl ferrocene dimethylcarboxamide, acetyl ferrocene, propoyl ferrocene, butyryl ferrocene, pentanoyl ferrocene, hexanoyl ferrocene, octanoyl ferrocene, benzoyl ferrocene, 1,1'-diacetyl ferrocene, 1,1'-dibutyryl ferrocene, 1,1'-dihexanoyl ferrocene, ethyl ferrocene, propyl ferrocene, n-butyl ferrocene, pentyl ferrocene, hexyl ferrocene, 1,1'-diethyl ferrocene, 1,1'-dipropyl ferrocene, 1,1'-dibutyl ferrocene, 1,1'-dihexyl ferrocene, cyclopentenyl ferrocene, cyclohexenyl ferrocene, 3-ferrocenoyl propionic acid, 4-ferrocenoyl butyric acid, 4-ferrocenylbutyric acid, 5-ferrocenylvaleric acid, 3-ferrocenoyl propionic acid esters, 4-ferrocenoyl butyric acid esters, 4-ferrocenyl butyric acid esters, 5-ferrocenylvaleric acid esters, dimethylaminomethyl ferrocene, 1,1 dicarboxyferrocene, carboxyferrocene, and vinyl-ferrorcene; porphyrin derivitives such as hydroporphyrins, chlorins, bacteriochlorins, isobacteriochlorins, decahydroporphyrins, corphins, porphyrins phthalocyanine, pyrrocorphin, and metal-complexed porphyrins including Magnesium porphyrin, Zinc porphyrin, and Iron porphyrin; quinone derivitives such as 2,5-dichloro-1,4-benzoquinone, Methylene Blue, Methyl-1, 4-benzoquinone, Anthraquinone, and 1,4-dihydroquinone; 1,4-dihydroxy-2-naphthoic acid; nanoparticles such as CdS anparticle and ZnS nanoparticles. Ji et al, J Phys. Chem. C, 2007, 111, 1496; Levine et al, Biosensors and Bioelectronics, 2009, 24, 1995.

Table 1 below shows some redox labels and their detection voltages:

TABLE 1

| Name | Detection Voltage |
| --- | --- |
| 1,4-dihydroquinone, | +0.9 volts v Ag/AgCl |
| 1,4-dihydroxy-2-naphthoic acid | both +0.6 and +0.9 v Ag/AgCl |
| Ferrocene | +0.2 v Ag/AgCl |
| 2,5-dichloro-1,4-benzoquinone | both −0.2 and −0.4 v Ag/AgCl |
| Methylene Blue | −0.3 v Ag/AgCl |
| Methyl-1,4-benzoquinone | −0.4 v Ag/AgCl |
| Anthraquinone | −0.5 v Ag/AgCl |
| CdS nanoparticle | −0.7 v Hg/Hg$_2$Cl$_2$ |
| ZnS nanoparticle | −1.1 v Hg/Hg$_2$Cl$_2$ |

In the methods of the invention, the redox label is repeatedly reduced and oxidized. In some cases, the charge state of the redox label will be different in the reduced and the oxidized state. For example, upon reduction, a label could go from being neutral to negatively charged, from positively charged to neutral, or for example from having a −2 charge to having a −3 charge. In some cases, a redox label that can be oxidized or reduced by more than one electron is used, e.g. a redox label that is reduced or oxidized by 2, 3, 4, or more electrons. In some cases, the linker and redox label will have enough total charge that the change in charge state will have a negligible effect on the behavior of the redox label.

Typically the redox labels on substantially all of a given type of nucleotide analog are in the reduced state, or the redox labels on substantially all of a given type of nucleotide analog are in the oxidized state. Where the two electrode configuration is used, one of the electrodes will therefore have more noise due to freely diffusing redox label than the other electrode. For example, in a reaction mixture where the pool of unreacted redox label 1 is in the reduced state, then if nucleotide analog 1 with redox label 1 diffused near the oxidizing electrode of the redox device without associating with the enzyme, it could be reduced, causing noise. However, if nucleotide analog 1 having redox label 1 diffused near the reducing electrode, no reaction would occur, and there would be no background noise created. Thus, in the two electrode configuration, by selection redox probes, one can produce a system in which one electrode has a higher signal-to-noise due to free diffusion of redox labels that the other electrode. Where this is the case, the base calling algorithms are implemented such that the information from the high signal to noise electrode is given higher weight in base calling. In some cases, all of the nucleotide analogs, e.g. all four of the nucleotide analogs, are added to the sequencing reaction mixture in the reduced state. In some cases, all of the nucleotide analogs, e.g. all four of the nucleotide analogs, are added to the sequencing reaction mixture in the oxidized state. In some cases, 1, 2, or 3 of the nucleotide analogs are added to the sequencing reaction mixture in the oxidized state and the others are added in the reduced state. In some cases, 1, 2, or 3 of the nucleotide analogs are added to the sequencing reaction mixture in the reduced state and the others are added in the oxidized state.

In some cases, for a given nucleotide analog, about half of the redox label is added in the reduced state and half in the oxidized state, whereby for that redox label, the signal to noise due to random diffusion of that nucleotide will tend to be equalized.

Typically four nucleotide analogs will be added and all four will have different redox labels. Having four labeled nucleotides is not required. For example 1, 2, 3, 4, or 5 nucleotides can be labeled with a redox label, either where each has a unique label or where the labels on some of the nucleotide analogs is the same. Where nucleotide analogs have the same label or have no label, it may be required that more than one sequencing run be carried out in order to obtain the complete sequence.

Kinetic Measurements—Modified Base Detection

The methods of the invention provide for measuring the incorporation of nucleotides into a growing chain in real time. The real time measurements allow for the determination of enzyme kinetics, which are can be sensitive to template characteristics such as secondary structure, and modified bases. The ability to detect modifications within nucleic acid sequences is useful for mapping such modifications in various types and/or sets of nucleic acid sequences, e.g., across a set of mRNA transcripts, across a chromosomal region of interest, or across an entire genome. The modifications so mapped can then be related to transcriptional activity, secondary structure of the nucleic acid, siRNA activity, mRNA translation dynamics, kinetics and/or affinities of DNA- and RNA-binding proteins, and other aspects of nucleic acid (e.g., DNA and/or RNA) metabolism.

In certain aspects of the invention, methods are provided for identification of a modification in a nucleic acid molecule using real time redox sequencing. In general, a template nucleic acid comprising the modification and an enzyme capable of processing the template are provided. The template nucleic acid is contacted with the enzyme, and the subsequent processing of the template by the enzyme is monitored. A change in the processing is detected, and this change is indicative of the presence of the modification in the template. Exemplary modifications that can be detected by the methods of the invention include, but are not limited to methylated bases (e.g., 5-methylcytosine, N6-methyladenosine, etc.), pseudouridine bases, 7,8-dihydro-8-oxoguanine bases, 2'-O-methyl derivative bases, nicks, apurinic sites, apyrimidic sites, pyrimidine dimers, a cis-platen crosslinking products, oxidation damage, hydrolysis damage, bulky base adducts, thymine dimers, photochemistry reaction products, interstrand crosslinking products, mismatched bases, secondary structures, and bound agents. In preferred embodiments, nucleotides or analogs thereof that are incorporated into a nascent strand synthesized by the enzyme are distinctly labeled to allow identification of a sequence of specific nucleotides or nucleotide analogs so incorporated. Labels are linked to nucleotides or nucleotide analogs through a phosphate group, e.g., a phosphate group other than the alpha phosphate group. As such, the redox labels are removed from the nucleotide or nucleotide analog upon incorporation into the nascent strand. Techniques for kinetically identifying modified bases are described, for example in U.S. Patent Application 20110183320 Classification of Nucleic Acid Templates which is incorporated herein by reference for all purposes.

The term "modification" as used herein is intended to refer not only to a chemical modification of a nucleic acids, but also to a variation in nucleic acid conformation or composition, interaction of an agent with a nucleic acid (e.g., bound to the nucleic acid), and other perturbations associated with the nucleic acid. As such, a location or position of a modification is a locus (e.g., a single nucleotide or multiple contiguous or noncontiguous nucleotides) at which such modification occurs within the nucleic acid. For a double-stranded template, such a modification may occur in the strand complementary to a nascent strand synthesized by a polymerase processing the template, or may occur in the displaced strand. Although certain specific embodiments of the invention are described in terms of 5-methylcytosine detection, detection of other types of modified nucleotides (e.g., $N^6$-methyladenosine, $N^3$-methyladenosine, $N^7$-methylguanosine, 5-hydroxymethylcytosine, other methylated nucleotides, pseudouridine, thiouridine, isoguanosine, isocytosine, dihydrouridine, queuosine, wyosine, inosine, triazole, diaminopurine, β-D-glucopyranosyloxymethyluracil (a.k.a., β-D-glucosyl-HOMedU, β-glucosyl-hydroxymethyluracil, "dJ," or "base J"), 8-oxoguanosine, and 2'-O-methyl derivatives of adenosine, cytidine, guanosine, and uridine) are also contemplated. Further, although described primarily in terms of DNA templates, such modified bases can be modified RNA bases and can be detected in RNA (or primarily RNA) templates. These and other modifications are known to those of ordinary skill in the art and are further described, e.g., in Narayan P, et al. (1987) Mol Cell Biol 7(4):1572-5; Horowitz S, et al. (1984) Proc Natl Acad Sci U.S.A. 81(18):5667-71; "RNA's Outfits: The nucleic acid has dozens of chemical costumes," (2009) C&EN; 87(36):65-68; Kriaucionis, et al. (2009) Science 324 (5929): 929-30; and Tahiliani, et al. (2009) Science 324 (5929): 930-35; Matray, et al. (1999) Nature 399(6737):704-8; Ooi, et al. (2008) Cell 133: 1145-8; Petersson, et al. (2005) J Am Chem Soc. 127(5):1424-30; Johnson, et al. (2004) 32(6):1937-41; Kimoto, et al. (2007) Nucleic Acids Res. 35(16):5360-9; Ahle, et al. (2005) Nucleic Acids Res 33(10):3176; Krueger, et al., Curr Opinions in Chem Biology 2007, 11(6):588); Krueger, et al. (2009) Chemistry & Biology 16(3):242; McCullough, et al. (1999) Annual Rev of Biochem 68:255; Liu, et al. (2003) Science 302(5646):868-71; Limbach, et al. (1994) Nuci. Acids Res. 22(12):2183-2196; Wyatt, et al. (1953) Biochem. J. 55:774-782; Josse, et al. (1962) J. Biol. Chem. 237:1968-1976; Lariviere, et al. (2004) J. Biol. Chem. 279:34715-34720; and in International Application Publication No. WO/2009/037473, the disclosures of which are incorporated herein by reference in their entireties for all purposes. Modifications further include the presence of non-natural base pairs in the template nucleic acid, including but not limited to hydroxypyridone and pyridopurine homo- and hetero-base pairs, pyridine-2,6-dicarboxylate and pyridine metallo-base pairs, pyridine-2,6-dicarboxamide and a pyridine metallo-base pairs, metal-mediated pyrimidine base pairs T-Hg(II)-T and C—Ag (I)-C, and metallo-homo-basepairs of 2,6-bis(ethylthiomethyl)pyridine nucleobases Spy, and alkyne-, enamine-, alcohol-, imidazole-, guanidine-, and pyridyl-substitutions to the purine or pyridimine base (Wettig, et al. (2003) J Inorg Biochem 94:94-99; Clever, et al. (2005) Angew Chem Int Ed 117:7370-7374; Schlegel, et al. (2009) Org Biomol Chem 7(3):476-82; Zimmerman, et al. (2004) Bioorg Chem 32(1): 13-25; Yanagida, et al. (2007) Nucleic Acids Symp Ser (Oxf) 51:179-80; Zimmerman (2002) J Am Chem Soc 124(46): 13684-5; Buncel, et al. (1985) Inorg Biochem 25:61-73; Ono, et al. (2004) Angew Chem 43:4300-4302; Lee, et al. (1993) Biochem Cell Biol 71:162-168; Loakes, et al. (2009), Chem Commun 4619-4631; and Seo, et al. (2009) J Am Chem Soc 131:3246-3252, all incorporated herein by reference in their entireties for all purposes). Other types of modifications include, e.g, a nick, a missing base (e.g., apurinic or apyridinic sites), a ribonucleoside (or modified ribonucleoside) within a deoxyribonucleoside-based nucleic acid, a deoxyribonucleoside (or modified deoxyribonucleoside) within a ribonucleoside-based nucleic acid, a pyrimidine dimer (e.g., thymine dimer or cyclobutane pyrimidine dimer), a cis-platin crosslinking, oxidation damage, hydrolysis damage, other methylated bases, bulky DNA or RNA base adducts, photochemistry reaction products, interstrand crosslinking products, mismatched bases, and other types of "damage" to the nucleic acid. As such, certain embodiments described herein refer to "damage" and such damage is also considered a modification of the nucleic acid in accordance with the present invention. Modified nucleotides can be caused by exposure of the DNA to radiation (e.g., UV), carcinogenic chemicals, crosslinking agents (e.g., formaldehyde), certain enzymes (e.g., nickases, glycosylases, exonucleases, methylases, other nucleases, glucosyltransferases, etc.), viruses, toxins and other chemicals, thermal disruptions, and the like. In vivo, DNA damage is a major source of mutations leading to various diseases including cancer, cardiovascular disease, and nervous system diseases (see, e.g., Lindahl, T. (1993) Nature 362(6422): 709-15, which is incorporated herein by reference in its entirety for all purposes). The methods and systems provided herein can also be used to detect various conformations of DNA, in particular, secondary structure forms such as hairpin loops, stem-loops, internal loops, bulges, pseudoknots, base-triples, supercoiling, internal hybridization, and the like; and are also useful for detection of agents interacting with the nucleic acid, e.g., bound proteins or other moieties.

In some embodiments, five color DNA sequencing can be carried out by the redox sequencing methods of the invention. Five color sequencing generally utilizes a nucleotide analog having a base that preferentially associates with a fifth base in the template or an abasic site. Such five color sequencing is described for example in U.S. Patent Application 20110183320, which is incorporated herein by reference in its entirety for all purposes.

Monitoring Biological Reactions

While the nanoscale redox devices and systems of the invention are described throughout most of this application for use in nucleic acid sequencing, it is to be understood that the devices and systems can also find use in other analytical reactions including monitoring biological reactions in real time, in particular monitoring the interactions of biological molecules at the single molecule level. The ability to analyze such reactions provides an opportunity to study those reactions as well as to potentially identify factors and/or approaches for impacting such reactions, e.g., to stimulate, enhance, or inhibit such reactions.

The invention provides for observation of the interaction of two or more specifically interacting reactants at the single molecule (or single molecular complex) level in order to monitor the progress of the interaction separately from other interactions. In other words, a single immobilized reaction component can be monitored at a single reaction site on a support such that redox signals received from that reaction site are resolvable from other immobilized reaction components at other reaction sites on that support. In preferred embodiments, the methods monitor redox detectable labels with a nanoscale redox device, such that a single reactant comprising a redox detectable label is distinguishable from a different single reactant comprising a different redox detectable label. A plurality of analytical reactions may also be carried out in an array of redox devices. Analytical reactions in an array of redox devices can be carried out simultaneously, and may or may not be synchronized with one another. In such an array, multiple reactions can therefore be monitored simultaneously and independently.

The monitoring typically comprises providing the interaction with one or more signaling events that are indicative of one or more characteristics of that interaction. Such signaling events may comprise the retention of a redox labeled reactant proximate to a given redox device. For example, in some embodiments, the labels provide redox signals that are detected by a redox detection system operably linked to a reaction site at which the analytical reaction is taking place. As used herein, a reaction site is a location on or adjacent to a substrate at which an analytical reaction is monitored, and may refer to, e.g., a position on the substrate at which one or more components of an analytical reaction are immobilized or to a "detection volume" within which an analytical reaction is monitored. The detected signals are analyzed to determine one or more characteristics of the analytical reaction, e.g., initiation, termination, affinity, biochemical event (e.g., binding, bond cleavage, conformational change, etc.), substrate utilization, product formation, kinetics of the reaction (e.g., rate, time between subsequent biochemical events, time between the beginning/end of subsequent biochemical events, processivity, error profile, etc.), and the like.

These characteristics may generally be broken into two categories: reactant characteristic(s) and interaction characteristic(s). Reactant characteristic(s) includes characteristics of a particular reactant, e.g., type/identity of reactant, concentration of the reactant, a label on the reactant, etc. Interaction characteristic(s) includes characteristics of a given interaction between multiple reactants, e.g., rates, constants, affinities, etc., and is typically determined based on reaction data gathered during such an interaction. For example, some characteristics of a polymerization reaction include the identity of a monomer incorporated into a growing polymer, the rate of incorporation, length of time the polymerase is associated with the template, and the length of the polymer synthesized. In some embodiments, various different components of an analytical reaction (e.g., different types of monomers) are differentially labeled to allow each labeled component to be distinguished from other labeled components during the course of the reaction. For example, incorporation of monomer A into a polymer can be distinguished from incorporation of monomer B.

In certain preferred embodiments, multiple characteristics of a reaction are monitored and/or determined. For example, these may be multiple characteristics of one or more reaction components (e.g., identity, concentration, etc.; "reactant characteristic(s)"), one or more characteristics of an interaction between two or more reaction components (e.g., related to product formation, kinetics of the reaction, binding or dissociation constants, etc.; "interaction characteristic(s)"), or, preferably, a combination reactant characteristic(s) and interaction characteristic(s).

In some embodiments, a reaction mixture comprises a plurality of types of non-immobilized binding partners, and a characteristic determined is the particular type of one of the non-immobilized binding partners, e.g., that associates with a particular reaction site. Typically, the redox label is attached to the non-immobilized through a linking group as described herein such that the redox label on the non-immobilized binding partner will be repeatedly oxidized and reduced when it is interacting with the immobilized binding partner that is immobilized proximate to a redox electrode. In some embodiments, an array of reaction sites comprises a plurality of types of immobilized binding partners, each at a different reaction site, and a characteristic is determined that identifies which type of immobilized binding partner is located at each of the different reaction sites. In some embodiments, an array of reaction sites comprising a plurality of types of immobilized binding partners, each at a different reaction site, is contacted with a reaction mixture comprising a plurality of types of non-immobilized binding partners; characteristics determined during the reaction serve to both identify which of the types of immobilized binding partners is located at each reaction site and which of the types of non-immobilized binding partners associate with the immobilized binding partners. In some cases, the specificity of the interaction between the non-immobilized and immobilized binding partners is high enough that detection of a label on a non-immobilized binding partner residing at a particular reaction site is sufficient to identify the immobilized binding partner at that reaction site. In some embodiments, a characteristic is determined that quantifies a particular aspect of an interaction between reaction components, e.g., affinity between an immobilized binding partner and a non-immobilized binding partner, a rate of catalysis of a reaction, or other aspects of the interaction. In some cases, different redox signaling events (e.g., different redox labels on one or more reaction components) are used to monitor or determine different characteristics of a reaction under observation, but in some embodiments a single redox signaling event can provide more than one type of characteristic information. For example, if a non-immobilized binding partner has a redox label that not only identifies it from a plurality of different non-immobilized binding partners, but also provides kinetic information about the reaction based on various parameters monitored in real time, e.g., the time it takes for binding to occur, the time it remains associated with the reaction site, the on/off rate, etc.

In some embodiments, multiple different interactions or reactions can occur and be monitored simultaneously or sequentially, where each individual interaction is monitored separately from every other, e.g. in a redox device, such that there is resolution between different interactions under observation. For example, multiple different non-immobilized reaction components may simultaneously or sequentially interact with an immobilized reaction component; e.g., the multiple different non-immobilized reaction components can be different non-immobilized binding partners for an immobilized binding partner, or different agents that may alter an interaction between two reaction components, or different monomers for incorporation into a polymer being synthesized at the reaction site. In other embodiments, an interaction between a non-immobilized reaction component and a product of a synthesis reaction occurs during the synthesis reaction, e.g., once the product is suitable for such interaction. For example, the product may need to be of a certain length, or in a certain conformation (e.g., in a particular higher-order structure) to be suitable for interaction with the non-immobilized reaction component. Alternatively, a synthesis reaction can be performed at a reaction site, and subsequently exposed to a reaction mixture comprising non-immobilized reaction components that can then interact with the product of the synthesis reaction, which is preferably immobilized at the reaction site. In preferred embodiments, the synthesis reaction is monitored to determine characteristics of the product (e.g., length, chemical composition, etc.) being synthesized. Knowledge of characteristics of the product of synthesis combined with the detection of an interaction with a particular reaction component provides additional characteristics, e.g., the binding site for the particular reaction component. Examples of biological interactions that can be measured with the redox devices and systems of the invention are described, for example, in U.S. 20100323912 Patent Application Real-Time Analytical Methods and Systems which is incorporated herein by reference for all purposes.

Systems

In some aspects, the invention provides systems for carrying out real time redox sequencing. A redox measuring system is used to monitor the working electrode over time allowing for the determination of whether a redox label is associating with the enzyme. That is, the working electrode and enzyme are configured such that the redox labeled nucleotide analogs in the solution are not substantially detected at the working electrode. Only when a redox label is brought into the vicinity of the working electrode due to its association with the polymerase enzyme is the label detected. One distinction between the freely diffusing nucleotide analogs and an analog in the active site of the enzyme is the amount of time spent proximate to the working electrode. Diffusing nucleotide analogs will be quickly diffusing in and out of the vicinity of the working electrode, while the nucleotide analog to be incorporated will spend a longer amount of time, for example on the order of milliseconds proximate to the working electrode. Thus, the redox measuring system will detect the presence of a nucleotide analog which is to be incorporated into the growing nucleic acid chain while it is in the active site of the enzyme. When the nucleotide is incorporated into the growing strand, the redox label, which is attached to the phosphate portion of the nucleotide analog is cleaved and diffuses away from the enzyme and the electrode. Thus, the redox measuring system determines the presence of the analog in the active site prior to incorporation. In addition, the identity of the distinct label is determined, e.g. by the value of the redox potential. As the polymerase reaction continues and is monitored by the redox measuring system, the sequence of the template nucleic acid can be determined by the time sequence of incorporation of the complementary nucleotide analog into the growing nucleic acid strand.

The systems of the invention include a chip comprising an array of nanoscale redox devices as described herein that is reversibly mated with other system components. The chip with array of nanoscale redox devices can be a single use chip or the chip can be used multiple times. The system typically has a housing into which the chip is placed. The housing has electrical connectors that provide reversible connections to the electrical connections on the chip. Sockets that provide reliable reversible electrical connections to chips inserted into the socket are well known. Electrical connections to the top, sides, bottom, or a combination of these sides can be used.

When the chip is inserted into the housing, the system provides a fluid reservoir to which fluid comprising the sequencing reaction mixture is added. In some cases, the fluid reservoir is included as part of the chip. In some cases, part of the fluid reservoir is associated with the housing, such that the insertion of the chip forms the reservoir. The fluid reservoir can be, for example a well or a chamber into which fluid can be introduced. The introduced fluid sequencing reaction mixture comes into contact with the redox devices on the surface of the chip. The system will typically include environmental control components including temperature control and control of a vapor phase above the fluid. The chemical makeup and the temperature of the vapor can be controlled, for example by providing a flow of inert gas over the reaction mixture to minimize oxidation of the sample. In some cases the system can have fluid handling systems for delivering and removing components to the fluid reservoir before, during, or after performing the sequencing reaction.

The fluid reservoir will also provide contact of the sequencing reaction mixture with either or both a reference electrode or counter electrode. As described above, in order to carry out the method, in some cases a reference electrode, a counter electrode, or both are used. In some one or more of these electrodes are on the chip. Where the reference electrode and/or counter electrode are used, and not on the chip, they are brought into contact with the sequencing reaction mixture in the fluid reservoir. The reference electrode can comprise, for example, a silver/silver chloride reference electrode.

Connected to the chip through the connectors on the housing are a current/voltage source and a meter. The source provides the current and voltage to bring the electrodes to the proper voltage over time to carry out the methods of the invention. The meter is used to measure the electrical current due to redox reactions at the electrode. In some cases, the source and meter are combined into a single unit. In some cases each of the redox devices in the array on the chip are addressed by a separate source and separate meter component within the system. In some cases, a single source can drive multiple redox devices. In some cases a single source will drive all of the redox devices on a chip, while each of the redox devices is measured with a separate meter component.

A computer control and analysis system is used to control both the input voltages and currents and to provide computer-implemented control functions, e.g., controlling the robotics, environmental conditions, and the state of various components of the system. The computer control system also includes components for computational data analysis (e.g., for single molecule sequencing applications, determining and characterizing nucleotide incorporation events). As described above, in some cases, some of the control functions can be implemented on the chip, in particular controlling source wave functions, or handling electrical signals from the redox devices on the chip. In some cases the computer control and analysis system provides substantially all of the control of the signals to and from the chip, and the chip simple acts as a redox device from which redox current data is extracted. In some cases, the chip can take on some of the functionality of control and analysis. The chip can process the analog data from the redox devices. The chip can also have analog to digital components, and can perform analysis and storage functions for the digital signals. The decision on how much functionality is implemented on the chip and how much is retained with the computer control and analysis system can be made based on the relative functionality gained versus the cost of adding the functionality.

Also provided is a user interface operatively coupled to the components for computational data, permitting a user of the system to initiate and terminate an analysis, control various parameters (e.g., with respect to analysis conditions, sequencing reaction mixture environment, etc.), and manage/receive data (e.g., nucleic acid sequence data) obtained by the system. In some aspects, the user interface is attached the computer control and analysis system. Additionally, remote user interfaces can be provided that are in communication with the overall system via a wireless network. Such user input devices may include other purposed devices, such as notepad computers, e.g., Apple iPad, or smartphones running a user interface application. Optionally, the user interface includes a component, e.g., a data port, from which the user can receive data obtained by the analysis system to a portable electronic storage medium for use at location other than the location of the substrate analysis system.

Aspects of the present invention are directed to machine or computer implemented processes, and/or software incorporated onto a computer readable medium instructing such processes. As such, signal data generated by the reactions and systems described above, is input or otherwise received into a computer or other data processor, and subjected to one or more of the various process steps or components set forth herein. Once these processes are carried out, the resulting output of the computer implemented processes may be produced in a tangible or observable format, e.g., printed in a user readable report, displayed upon a computer display, or it may be stored in one or more databases for later evaluation, processing, reporting or the like, or it may be retained by the computer or transmitted to a different computer for use in configuring subsequent reactions or data processes.

Computers for use in carrying out the processes of the invention can range from personal computers such as PC or Macintosh® type computers running Intel Pentium or Duo-Core processors, to workstations, laboratory equipment, or high speed servers, running UNIX, LINUX, Windows®, or other systems. Logic processing of the invention may be performed entirely by general purposes logic processors (such as CPU's) executing software and/or firmware logic instructions; or entirely by special purposes logic processing circuits (such as ASICs) incorporated into laboratory or diagnostic systems or camera systems which may also include software or firmware elements; or by a combination of general purpose and special purpose logic circuits. Data formats for the signal data may comprise any convenient format, including digital image based data formats, such as JPEG, GIF, BMP, TIFF, or other convenient formats, while video based formats, such as avi, mpeg, mov, rmv, or other video formats may be employed. The software processes of the invention may generally be programmed in a variety of programming languages including, e.g., Matlab, C, C++, C#, NET, Visual Basic, Python, JAVA, CGI, and the like.

While described in terms of a particular sequencing by incorporation process or system, it will be appreciated that certain aspects of the processes of the invention may be applied to a broader range of analytical reactions or other operations and varying system configurations than those described for exemplary purposes.

In-Situ Purification of Nucleotides Via Electrodic Ionization

Another aspect of the invention is in-situ purification of nucleotides via electrodic ionization. Methods that rely on downstream detection of cleaved nucleotides in single-molecule sequence face an inherent issue that nonspecifically hydrolyzed nucleotides can show up as incorporation events. For example, in one embodiment, an activatable redox cycling reagent such as aminophenoxyphospho-dNTP is contacted with a polymerase leading to incorporation events that liberate aminophenoxyphsophate. When this compound is activated by phosphatase to generate aminophenol, we now have a redox active compound in solution that can be detected now even to the single molecule level. However, one problem with the method is that nonspecific hydrolysis of nucleotide in the bulk solution can generate free aminophenoxyphosphate in solution that is prone to activation and is then indistinguishable from material that was created by DNA synthesis, leading to insertion errors. The current invention contemplates a solution to this problem.

In some aspects the invention provides a method wherein, upstream of the reaction chamber containing the DNA polymerase, we place an electrode disposed at such a potential as to be able to reduce an oxidized tag or to oxidize a reduced tag. For example, we chose to oxidize a reduced tag. (the analogous method can be practiced by reducing an oxidized tag). This oxidation can be carried out so as to leave the tag positively charged. The oxidizing electrode is positioned so as to surround the entrance to the reaction chamber. In this way, it is difficult or impossible for a nucleotide to enter the reaction chamber without contacting the oxidizing electrode. Then the reaction chamber is held at a potential higher than the region outside, so that positively charged ions are rejected from the opening and travel the wrong way, while molecules with a net negative charge move into the reaction chamber for incorporation.

In this way materials that have been nonspecifically hydrolyzed will not participate in the detection process, as they will be electrophoretically biased away from the reaction chamber.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. For example, particle delivery can be practiced with array well sizing methods as described. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

The structures described here can be made using semiconductor processing to produce substrates having thousands to millions of independently redox measuring systems to allow for high throughput. The system can be multiplexed, ether on an open, flat surface, or on a more complex geometry, such as channels that can carry sample.

The surfaces are differentially modified using known chemistry to 1) put the polymerase complex at the appropriate position proximate to the working electrode, 2) reduce non-specific binding of unwanted components, and 3) to suppress electro-osmotic flows and electrolysis.

EXAMPLES

Example 1

Real-Time Redox Sequencing

A redox sequencing chip is produced having nine separate nano-electrode redox pairs. Onto a silicon substrate is deposited, patterned, and etched a first layer of platinum, a layer of $SiO_2$, a second layer of platinum, and a layer of silicon nitride. This process produces a substrate having nine nano-electrode pairs having electrical interconnects extending to the edge of the silicon substrate as shown in FIG. 5. The thickness of the $SiO_2$ layer is about 4 nanometers. The thickness of the platinum electrode layers is about 10 nanometers. The electrical interconnects provide for connecting the nano-electrodes to the off-chip electronics.

After surface treatment of the chip with an oxygen plasma and washing, the chip is chemically treated to specifically bias the surface for selective attachment of a polymerase enzyme to the $SiO_2$ layer between the nanoscale electrodes as described in U.S. Pat. No. 8,193,123. The chip is treated with a solution of silane-PEG-biotin in order which preferentially provides surface attached biotin to the $SiO_2$ layer between the electrodes.

Lambda DNA is fragmented, and hairpin adaptors s are ligated to the ends of the fragments to produce a library of circular templates each having a complementary double stranded region closed on each end with a hairpin as described in U.S. Pat. No. 8,153,375. A primer is added to the library that hybridizes with a region within the hairpin adaptor to provide a primed DNA library.

A phi-29 DNA polymerase selected for carrying out DNA synthesis at rates appropriate for detection is prepared as described in U.S. Patent Application 20110189659. The DNA polymerase has a biotin tag sequence as described in U.S. Patent Application 20110306096. The DNA polymerase is treated with an excess of streptavidin in order to produces a solution of DNA polymerase-streptavidin. The DNA polymerase-streptavidin is mixed with the library of primed circular DNA constructs under conditions whereby a library of polymerase-template complexes is formed.

The redox sequencing chip is mounted within a redox sequencing system such that a reservoir is formed above the chip allowing for the introduction of a sequencing solution which comes into contact with the nano-electrode pairs on the chip. The redox sequencing system has socket with receives the sequencing chip such that the electrical interconnects on the chip mate with connectors on the socket to allow for conducting electrical signals to and from the nano-electrodes, which form the working electrodes for electrochemical measurements with the system.

The library of polymerase template complexed is diluted and applied to the substrate such that the streptavidin on the polymerase binds to the biotin groups attached to the $SiO_2$ layer between the nano-electrodes. The level of dilution is chosen such that at least some of the nano electrode pairs has a single enzyme bound to it. This can be done by serial dilution. Poisson statistics suggests that more than a third of the nanoelectrode pairs will have a single polymerase bound at the optimal dilution level.

Figure 12:
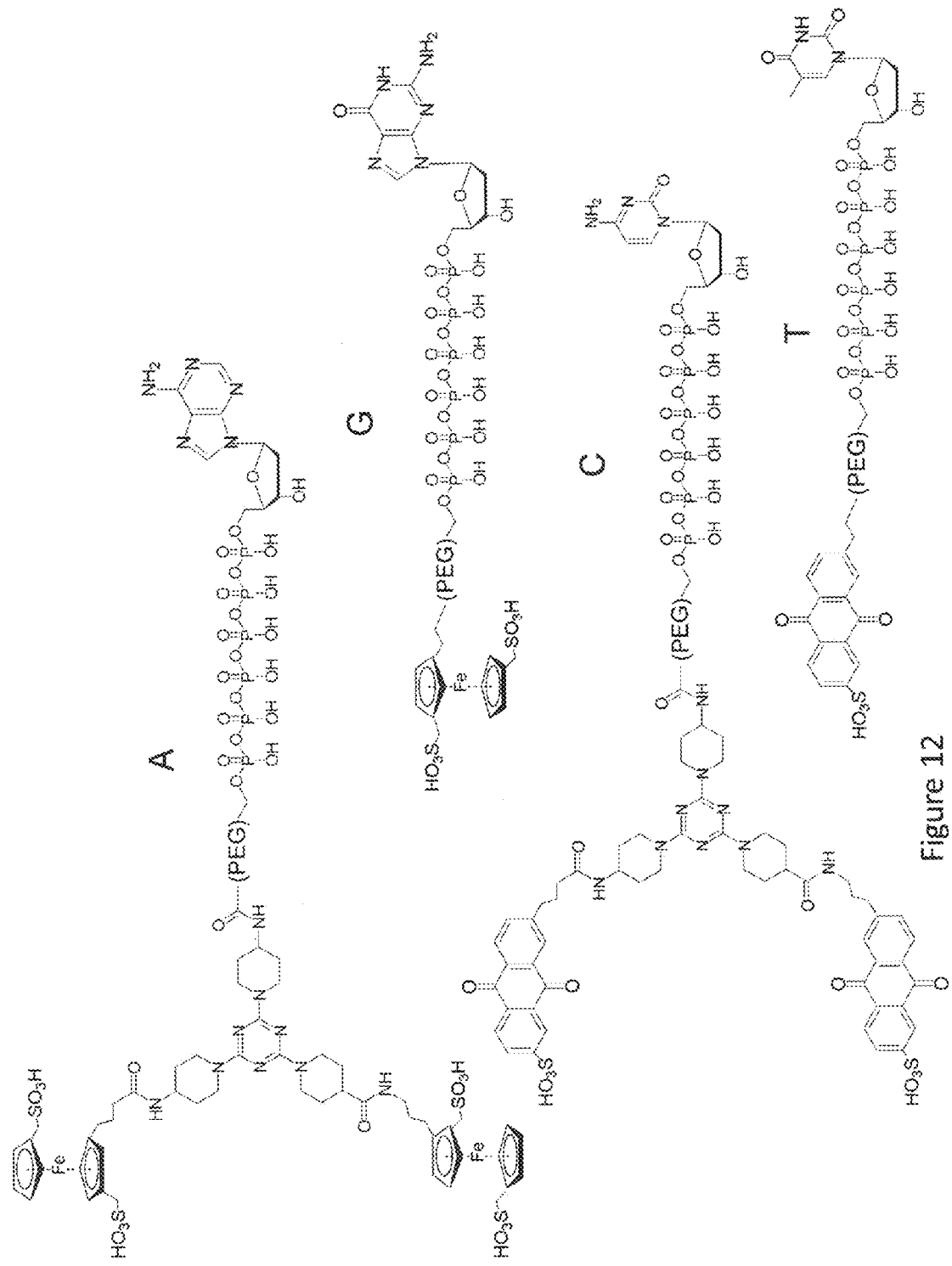
FIG. 12 shows an exemplary set of nucleotide analogs corresponding to nucleotides A, G, C, and T providing four differentiable redox labels using two different redox active species.

A sequencing solution is added to the reservoir such that the sequencing system is in contact with the chip, and in contact with a calomel reference electrode. In some cases, a counter electrode in contact with the sequencing solution is also used. The sequencing solution has the components required for polymerase activity as well as having ions at the levels required for accurately measuring the electrochemical properties of the system. The solution has potassium ions to maintain the appropriate electrolytic levels, and has Mg++ or Mn++ as required for the activity of the polymerase enzyme. The sequencing solution also has four differently labeled nucleotide analogs shown in FIG. 12. Each of the analogs has a nucleotide portion comprising a hexaphosphate, a deoxy ribose, and a nucleobase. Attached to the terminal phosphate of the nucleotide moiety is a polyethylene glycol (PEG) linker. The PEG linker has 77 PEG units and is connected to the redox label. The nucleotide analog corresponding to G has one ferrocene di(methyl sulfate) as a redox label. The nucleotide analog corresponding to A has two ferrocene di(methyl sulfate) labels, The nucleotide analog corresponding to T has one anthraquinone sulfate label, and the nucleotide analog corresponding to C has two anthraquinone sulfate labels. Anthraquinone sulfate and ferrocene di(methyl sulfate) can be distinguished due to their different redox potentials, and nucleotides having one redox label can be distinguished from nucleotides having two labels by the difference in amplitude of redox current.

As soon as all of the reagents required for nucleic acid synthesis, the polymerase enzyme proceeds to add nucleotides to the primer to produce a nascent strand. While a nucleotide analog to be incorporated is associated with the enzyme, the redox label is oxidized and reduced multiple times and thereby detected multiple times by the nano-electrode pair. Once a nucleotide from a nucleotide analog is added to the nascent strand, the label is cleaved and released.

Figure 11:
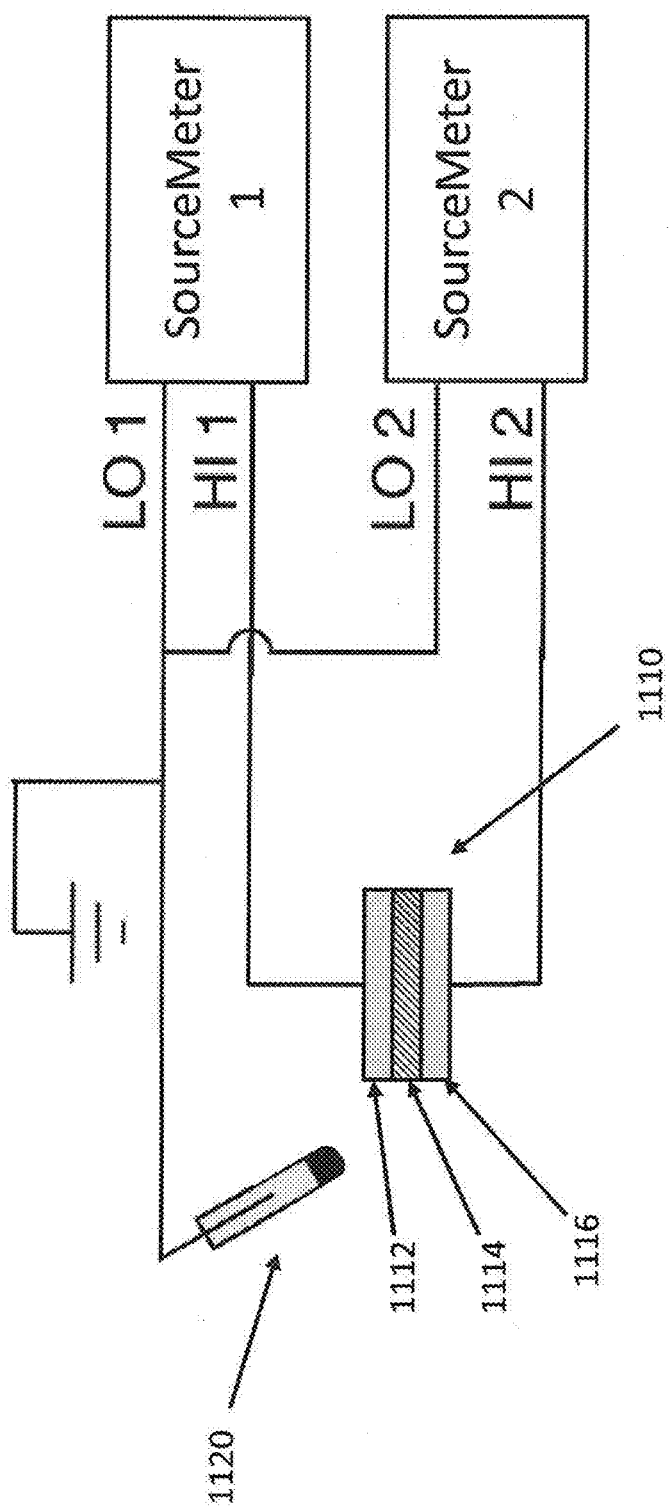
FIG. 11 shows the electrical connections between the redox device, the two source meters, and the reference electrode.

For electrical measurements, two sub-femtoamp remote SourceMeters are used both as voltage source to bias the electrodes and as current detection element. The wiring scheme is schematically shown in FIG. 11. The signal LO lines from both SourceMeters are short-circuited and connected to the Ag/Ag+ reference electrode 1120, while each of the signal HI lines is connected to one of the nano electrodes 1112 and 1116, which are separated by $SiO_2$ layer 1114. The signal LO lines are also connected to chassis ground of the SourceMeters. The instrument parameters are set for the best resolution. In some cases, the internal filtering of the instruments is set to 50 Hz, while the current range is 100 pA (corresponding to a nominal resolution of 1 fA).

In order to select the voltage profile for sequencing, an experiment is performed in which the voltage on the top nano-electrode and the bottom nano-electrode are swept. For example, voltage difference between the top electrode and the bottom electrode is fixed at 0.45 volts while the voltage is swept through as wide a range of voltages as is practical in light of oxidation and reduction events at low or high voltage such as solvent electrolysis. The current at the electrodes is monitored. In a typical experiment, two current peaks are observed one corresponding to the repeated reduction and oxidation of the ferrocene di(methyl sulfate) label and the other corresponding to the repeated oxidation and reduction of the anthraquinone sulfate label. The voltages corresponding to the peaks are then used for the sequencing experiment where, for example, voltage state 1 corresponds to the oxidation and reduction of ferrocene di(methyl sulfate), and voltage state 2 corresponds to the oxidation and reduction of anthraquinone sulfate.

For detection of sequencing, the SourceMeters alternatively supply one of two voltage states, voltage state 1 and voltage state 2. For voltage state 1, the top electrode is at top electrode voltage 1 and bottom electrode is at bottom electrode voltage 1 where the difference between these voltages is 0.45 volts. After a time, e.g. 500 microseconds, the voltage state 2 is applied, where the top electrode is at top electrode voltage 2 and the bottom electrode voltage is at bottom electrode voltage 2 where the difference between the voltages is 0.45 volts. Every 500 microseconds, the voltage is cycled between these voltage states resulting in a square wave with a frequency of 1 kHz. When a nucleotide analog is being incorporated into the growing strand, it is held in the enzyme active site, and therefore held near the electrodes, for a longer period of time than a diffusing species would spend near the electrodes. In some cases, the mean time in the active site for a nucleotide that is incorporated is 100 to 500 milliseconds. Peaks of current are observed for the period of time that the nucleotide analog is in the active site of the enzyme. Peaks during voltage state 1 correspond to the incorporation of A or G. The distinction between A and G is made on the basis of the amount of current observed. The incorporation of A results in a higher level of current due to the presence of twice as many redox active species proximate to the electrodes. Peaks during voltage state 2 correspond to C or T. The distinction between C and T is made on the basis of the amount of current observed. The incorporation of C results in a higher level of current due to the presence of twice as many redox active species proximate to the electrodes. During a given incorporation event, the voltage states are alternated hundreds of times. Having multiple points allows for improved signal to noise. The current data is combined into bins, where each bin is 10 milliseconds long, and divided into 20 sub-bins, each sub-bin corresponding to a voltage level. The 10 sub-bins corresponding to voltage state 1 are combined, and the 10 sub-bins corresponding to voltage state 2 are combined. Base calling software is then used to call incorporated bases using the combined current data from each bin as a 10 millisecond data point.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

We claim:

1. A system for sequencing a template nucleic acid comprising:
 a housing having housing electrical connection sites;
 a chip that reversibly mates with the housing comprising a substrate comprising:
  chip electrical connection sites that reversibly connect to the housing electrical connection sites;
  a plurality of redox devices, each redox device comprising at least one nanoscale redox electrode and a single polymerase enzyme complex bound to the at least one nanoscale redox electrode or to the substrate proximate to the at least one nanoscale redox electrode, wherein the polymerase enzyme complex comprises a polymerase enzyme and a template nucleic acid;
  a fluid reservoir comprising a sequencing reaction mixture in contact with the redox devices, the sequencing reaction mixture comprising a plurality of types of nucleotide analogs, each having a different redox label, wherein each redox label is connected to the nucleotide portion of the analog through a linker of a length whereby the redox labels are oxidized and reduced while an analog is associated with the polymerase enzyme complex;
 an electronic control system electrically connected to the nanoscale electrodes through the electrical connections to apply desired voltages to the nanoscale redox electrodes and for determining the current to and from the nanoscale redox electrodes; and
 a computer that receives information on the current to and from the nanoscale redox electrodes over time and uses such information to identify a sequence of the template nucleic acid.

2. The system of claim 1 wherein the substrate comprises greater than 1,000 redox devices.

3. The system of claim 1 wherein the substrate comprises greater than 10,000 redox devices.

4. The system of claim 1 wherein the substrate comprises about 1,000 redox devices to about 10 million devices.

5. The system of claim 1 wherein the substrate comprises about 10,000 redox devices to about 1 million devices.

6. The system of claim 1 wherein each nanoscale redox electrode is electrically connected to an electrical interconnection through which the electrode is brought to the appropriate voltage levels and through which the redox current is measured.

7. The system of claim 1 wherein the substrate comprises electronic elements for one or more of: providing current to bring the nanoscale electrodes to the desired voltages, measuring the redox current at the nanoscale electrodes, analog to digital conversion, signal processing, and data storage.

8. The system of claim 7 wherein the electrical elements are CMOS elements.

9. The system of claim 1 wherein the substrate comprises a plurality of counter electrodes.

10. The system of claim 9 wherein there is one counter electrode for each nanoscale redox device.

* * * * *